United States Patent [19]

Anderson et al.

[11] Patent Number: 5,614,533
[45] Date of Patent: Mar. 25, 1997

[54] SUBSTITUTED PIPECOLINIC ACID DERIVATIVES AS HIV PROTEASE INHIBITORS

[75] Inventors: Paul C. Anderson, Pierrefonds; François Soucy, Lachenaie; Christiane Yoakim, Laval; Pierre Lavallée, Rosemère; Pierre L. Beaulieu, Montréal, all of Canada

[73] Assignee: Bio-Mega/Boehringer Ingelheim Research, Inc., Laval, Canada

[21] Appl. No.: 336,637

[22] Filed: Nov. 9, 1994

Related U.S. Application Data

[63] Continuation of Ser. No. 25,703, Mar. 3, 1987, Pat. No. 4,764,598, which is a continuation-in-part of Ser. No. 850,716, Mar. 13, 1992, abandoned.

[51] Int. Cl.$^6$ .................. C07D 401/14; C07D 413/14; A61K 31/47; A61K 31/535; A61K 31/505
[52] U.S. Cl. .................. 514/314; 514/233.5; 514/256; 544/128; 544/333; 546/168; 546/169
[58] Field of Search .................. 546/168, 169; 514/314, 233.5, 256; 544/128, 333

[56] References Cited

FOREIGN PATENT DOCUMENTS

| | | |
|---|---|---|
| 2030415 | 6/1991 | Canada . |
| 0346847 | 12/1989 | European Pat. Off. . |
| 0352000 | 1/1990 | European Pat. Off. . |
| 0402646 | 12/1990 | European Pat. Off. . |
| 0432695 | 6/1991 | European Pat. Off. . |

OTHER PUBLICATIONS

Gallo et al., "AIDS in 1988", Sci. A 259(4): 40 (1988).
Norbeck et al., "HIV Protease Inhibitors", Ann. Reports in Med: Chem. 26:141 (1991).
Rich et al., "Hydroxyethylamine Analogues of the p17/p24 Substrate Cleavage Site are Tight–Binding Inhibitors of HIV Protease", J. Med. Chem. 33: 1285 (1990).
Roberts et al., "Rational Design of Peptide–Based HIV Proteinase Inhibitors", Science 248:358 (1990).
Overton et al., "Effects of Two Novel Inhibitors of the Human Immunodeficiency Virus Protease on the Maturation of the HIV gag and gag–pol Polyproteins", Virology 179: 508 (1990);.
Martin et al., "The Inhibitory Activity of a Peptide Derivative Against the Growth of Simiasn Immunodeficiency Virus in C8166 Cells", Biochem. Biophysio. Res. Com. 176:180 (1991).
Craig et al., "Efffects of a Specific Inhibitor of HIV Proteinase (Ro 31–8959) on virus maturation in a chronically infected promonocytic cell line (U1", Antiviral Chem. & Chemo.2(3):181 (1991).

*Primary Examiner*—David B. Springer
*Attorney, Agent, or Firm*—Robert P. Raymond; Alan R. Stempel; Mary-Ellen M. Devlin

[57] ABSTRACT

Disclosed herein are compounds of formula 1

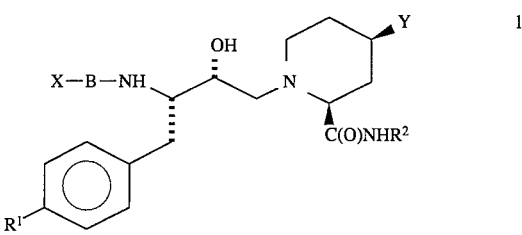

wherein X is a terminal group, for example, an aryloxycarbonyl, an alkanoyl or an optionally mono- or disubstituted carbamoyl; B is absent or an amino acid residue, for example, Val or Ash; $R^1$ is hydrogen or a ring substituent, for example, fluoro or methyl; $R^2$ is alkyl; and Y is a ring substituent, for example, phenoxy, 2-pyridinylmethoxy, phenylthio or 2-pyridinylthio. The compounds inhibit the activity of human immunodeficiency virus (HIV) protease and interfere with HIV induced cytopathogenic effects in human cells. These properties render the compounds useful for combating HIV infections.

9 Claims, No Drawings

SUBSTITUTED PIPECOLINIC ACID DERIVATIVES AS HIV PROTEASE INHIBITORS

This is a continuation of application Ser. No. 025,703, filed Mar. 3, 1993, U.S. Pat. No. 4,764,598, which is a continuation-in-part of application Ser. No. 850,716, filed Mar. 13, 1992, now abandoned.

FIELD OF INVENTION

This invention relates to compounds exhibiting activity against particular retroviruses, to processes for producing the compounds, to pharmaceutical preparations thereof, and to a method of using the compounds to combat infections caused by the retroviruses.

BACKGROUND OF THE INVENTION

In 1983, a retrovirus, known as human immunodeficiency virus type 1 (HIV-1), was established as a causative agent of acquired immune deficiency syndrome (AIDS), see R. C. Gallo and L. Montagnier, Scientific American, 259(4), 40 (1988). This virus has become a pestilence of alarming proportion. More recently, the closely related virus, human immunodificiency virus type 2 (HIV-2) has been identified as a second causative agent of AIDS.

The identification of human immunodeficiency virus (HIV) as a causative agent and the development of methods to grow the virus in quantity have resulted in the discovery of compounds which inhibit the replication of HIV in vitro. The most important class of inhibitor compounds identified in this manner is a group of dideoxynucleosides of which 3'-azido-3'-deoxythymidine (known also a zidovudine or AZT) and, more recently, 2',3'-dideoxyinosine (known also as didanosine or DDI) are used therapeutically to manage certain patients with symptomatic HIV infections. This class of compounds has been found to interfere with the life cycle of HIV by inhibiting reverse transcriptase. This enzyme converts viral RNA to double-stranded deoxyribonucleic acid (DNA) and as such is an essential enzyme for HIV replication. In addition to inhibiting reverse transcriptase, other stages of the HIV life cycle have been identified as targets for developing anti-AIDS drugs. One target that is receiving increased attention is an HIV-encoded enzyme known as HIV protease. This enzyme, like the reverse transcriptase, is encoded by the pol gene and is essential for HIV growth. It is responsible for effecting certain cleavages within the gag (p55) or gag-pol (p180) proteins to release structural proteins, e.g. p17 and p24, and enzymes, including itself, found in mature infectious virions. Thus, inhibitors of HIV protease can block the HIV life cycle.

The increased attention given to HIV protease over the last few years is reflected in the increase in reports of the discovery of agents which block the enzyme. See, for example, the recent review on protease inhibitors by D. W. Norbeck and D. J. Kempf, Annual Reports In Medicinal Chemistry, 26, 141 (1991). As noted in the latter review and reported by D. H. Rich et al., J. Med. Chem., 23, 1285 (1990) and N. A. Roberts et al., Science, 248, 358 (1990), two potent series of HIV protease inhibitors have been realized by the placement of a hydroxyethylamine transition state analog (TSA) in a peptide having the p17/p24 substrate cleavage site sequence. Biological investigations of lead compounds of the Roberts et al. series have been reported by H. A. Overton et al., Virology, 179, 508 (1990), J. A. Martin et al., Biochem. Biophys. Res. Commun., 176, 180 (1991) and J. C. Craig et al., Antiviral Chemistry and Chemotheraphy, 2, 181 (1991).

Other disclosures of HIV protease inhibitors having a hydroxyethylamine TSA include:

- B. K. Handa et al., European patent application 346 847, published Dec. 20, 1989,
- G. B. Dreyer et al., European patent application 352 000, published Jan. 24, 1990,
- D. J. Kempf et al., European patent application 402 646, published Dec. 19, 1990,
- K. E. B. Parkes et al., Canadian patent application 2,030, 415, published Jun. 12, 1991, and
- J. A. Martin and S. Redshaw, European patent application 432 695, published Jun. 19, 1991.

The present application discloses pipecolinic acid derivatives having an ethylamine TSA incorporated therein. The derivatives are potent inhibitors of HIV protease. Moreover, a capacity to inhibit HIV induced cytopathogenic effects in human cells has been demonstrated for the compounds. Such properties, together with the attributes of a relatively selective action and an apparent lack of toxicity, renders the compounds useful as agents for combating HIV infections.

SUMMARY OF THE INVENTION

The compounds of this invention are represented by formula 1

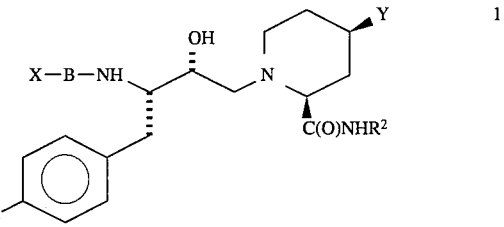

wherein

X is $R^3OC(O)$, $R^3C(O)$ or $R^3NR^4C(O)$ wherein $R^3$ is
(i) lower alkyl,
(ii) lower cycloalkyl,
(iii) phenyl; phenyl monosubstituted with halo, hydroxy, lower alkyl or lower alkoxy; or disubstituted phenyl wherein each of the two substituent is independently lower alkyl or halo;
(iv) phenyl(lower)alkyl or phenyl(lower)alkyl wherein the aromatic portion thereof is monosubstituted with halo, hydroxy, lower alkyl or lower alkoxy,
(v) 1-naphthyl or 2-naphthyl,
(vi) (Het) or (Het)-(lower alkyl) wherein Het represents a five or six membered, monovalent heterocyclic radical containing one or two hetero
atoms selected from nitrogen, oxygen and sulfur, or
(vii) 2-quinolinyl or 3-quinolinyl, and $R^4$ is hydrogen or lower alkyl; or X is $R^{3A}OCH_2C(O)$ wherein $R^{3A}$ is phenyl or monosubstituted, disubstituted or trisubstituted phenyl wherein each substituent is independently lower alkyl or halo;

B is absent or the divalent radical —$NHCHR^5C(O)$— wherein $R^5$ is lower alkyl; lower cycloalkyl; (lower cycloalkyl)-(lower alkyl); phenylmethyl; or lower alkyl monosubstituted with hydroxy, carboxy, lower alkoxycarbonyl, aminocarbonyl, (lower alkyl)aminocarbonyl carbonyl or di(lower alkyl)aminocarbonyl;

$R^1$ is hydrogen, halo, hydroxy, lower alkyl or lower alkoxy;

$R^2$ is lower alkyl; and

Y is lower alkyl; lower cycloalkyl; phenyl or phenyl monosubstituted with halo, hydroxy, lower alkyl or lower alkoxy; phenylmethyl or phenylmethyl monosubstituted with halo, hydroxy, lower alkyl or lower alkoxy; or Y is $W(CH_2)_nZ$ wherein W is oxo, thio, sulfinyl or sulfonyl, Z is lower alkyl; phenyl or phenyl monosubstituted with halo, hydroxy, lower alkyl or lower alkoxy; or (Het) wherein (Het) is as defined hereinbefore; and n is zero or one;

or a therapeutically acceptable acid addition salt thereof.

It is to be understood that the term "B is absent", used herein with reference to formula 1, means that the symbol B has become a covalent bond joining "X" to the secondary amino group which otherwise would be joined to "B".

A preferred group of compounds of the invention is represented by formula 1 wherein X is $R^3OC(O)$, $R^3C(O)$ or $R^3NR^4C(O)$ wherein $R^3$ is lower alkyl, phenyl, 2,4-dimethylphenyl, 2,6-dimethylphenyl, 2,4-dichlorophenyl, 2,5-dichlorophenyl, 2,6-difluorophenyl, 5-fluoro-2-methylphenyl, phenyl(lower)alkyl, phenyl(lower)alkyl wherein position 4 of the phenyl portion is substituted with chloro, fluoro, hydroxy, methyl or methoxy, 1-naphthyl, 2-naphthyl, 2-furyl, 2-thienyl, 2-pyridinyl, 4-pyridinyl, 2-pyridinylmethyl, 4-thiazolylmethyl or 2-quinolinyl, and $R^4$ is hydrogen or lower alkyl; or X is $R^{3A}OCH_2C(O)$ wherein $R^{3A}$ is phenyl or phenyl mono-, di- or trisubstituted with lower alkyl or halo at a position or positions selected from the group consisting of positions 2, 4 and 6;

B is absent or is the divalent radical —$NHCHR^5C(O)$— wherein $R^5$ is lower alkyl, or lower alkyl monosubstituted with hydroxy, lower alkoxycarbonyl, aminocarbonyl, (lower alkyl)aminocarbonyl or di(lower alkyl)aminocarbonyl;

$R^1$ is hydrogen, chloro, bromo or fluoro;

$R^2$ is 1-methylethyl, 2-methylpropyl or 1,1-dimethylethyl; and

Y is lower cycloalkyl, phenyl, 4-chlorophenyl, 4-bromophenyl, 4-fluorophenyl, 4-methylphenyl, 4-methoxyphenyl, phenylmethyl, (4-fluorophenyl)methyl or (4-methylphenyl)methyl; or Y is $W(CH_2)_nZ$ wherein W and n are as defined hereinabove and Z is lower alkyl, phenyl, 2-furyl, 2-thienyl, 2-pyridinyl, 3-pyridinyl, 4-pyridinyl, 4-thiazolyl, 2-pyrimidinyl, 4-methyl-2-pyrimidinyl, 4,6-dimethyl-2-pyrimidinyl or 2,6-dimethyl-4-pyrimidinyl; or a therapeutically acceptable acid addition salt thereof.

A more preferred group of compounds is represented by formula 1 wherein X is tert-butyloxycarbonyl, (2,6-dimethylphenyl)carbonyl, (2,4-dichlorophenyl)carbonyl, (2,5-dichlorophenyl)carbonyl, (2,6-difluorophenyl)carbonyl, (5-fluoro-2-methylphenyl)carbonyl, benzyloxycarbonyl, (4-chlorophenyl)methoxycarbonyl, (4-hydroxyphenyl)methoxycarbonyl, (4-methoxyphenyl)methoxycarbonyl, acetyl, benzoyl, 1-naphthalenylcarbonyl, 2-naphthalenylcarbonyl, (2-pyridinylmethoxy)carbonyl, 2-quinolinylcarbonyl, benzylaminocarbonyl, N-(2-pyridinylmethyl)aminocarbonyl, N-methyl-N-(2-pyridinylmethyl)aminocarbonyl, phenoxyacetyl, (2-methylphenoxy)acetyl, (2,4-dimethylphenoxy)acetyl, (2,6-dimethylphenoxy)acetyl, (2,4,6-trimethylphenoxy)acetyl, (4-chlorophenoxy)acetyl or (4-fluoro-2,6-dimethylphenoxy)acetyl;

B is absent or the divalent radical —$NHCHR^5C(O)$— wherein $R^5$ is 1-methylethyl, 1,1-dimethylethyl, 1-methylpropyl, 2-methylpropyl, 1-hydroxyethyl, (methoxycarbonyl)methyl, (ethoxycarbonyl)methyl, (aminocarbonyl)methyl or {(methylamino)carbonyl}methyl; $R^1$ is hydrogen or fluorine; $R^2$ is 2-methylpropyl or 1,1-dimethylethyl; and Y is cyclohexyl, phenyl, 4-chlorophenyl, 4-fluorophenyl, 4-methoxyphenyl, benzyl, (4-methoxyphenyl)methyl, 2-methylpropoxy, phenoxy, 2-pyridinyloxy, 3-pyridinyloxy, 4-pyridinyloxy, 2-pyrimidinyloxy, (4-methyl-2-pyrimidinyl)oxy, (4,6-dimethyl-2-pyrimidinyl)oxy, (2,6-dimethyl-4-pyrimidinyl)oxy, benzyloxy, 2-pyridinylmethoxy, 3-pyridinylmethoxy, 4-pyridinylmethoxy, 4-thiazolylmethoxy, phenylthio, phenylsulfinyl, phenylsulfonyl, 2-pyridinylthio, 3-pyridinylthio, 4-pyridinylthio, 2-pyrimidinylthio, (4-methyl-2-pyrimidinyl)thio, (2,6-dimethyl-4-pyrimi-dinyl)thio, (4,6-dimethyl-2-pyrimidinyl)thio, benzylthio, benzylsulfinyl, benzylsulfonyl, (2-pyridinylmethyl)thio, (3-pyridinylmethyl)thio or (4-pyridinylmethyl)thio; or a therapeutically acceptable acid addition salt.

A most preferred group of the compounds is represented by formula 1 in which X is tert-butyloxycarbonyl, benzyloxycarbonyl, acetyl, (2,6-dimethylphenyl)carbonyl, 2-naphthalenylcarbonyl, (2-pyridinylmethoxy)carbonyl, 2-quinolinylcarbonyl or {N-methyl-N-(2-pyridinylmethyl)amino}carbonyl; B is valyl, tert-butylglycyl, isoleucyl, threonyl or asparaginyl; $R^1$ is hydrogen or fluorine; $R^2$ is 1,1-dimethylethyl; and Y is phenyl, benzyl, phenoxy, 2-pyrimidinyloxy, (2,6-dimethyl-4-pyrimidinyl)oxy, 2-pyridinylmethoxy, 3-pyridinylmethoxy, 4-pyridinylmethoxy, phenylthio, phenylsulfinyl, phenylsulfonyl, 2-pyridinylthio, 3-pyridinylthio, 4-pyridinylthio, 2-pyrimidinylthio (4,6-dimethyl-2-pyrimidinyl)thio, (2-pyridinylmethyl)thio, (3-pyridinylmethyl)thio or 4-(pyridinylmethyl)thio; or a therapeutically acceptable acid addition salt thereof.

Another most preferred group of compounds is represented by formula 1 wherein X is (2-methylphenoxy)acetyl, (2,4-dimethylphenoxy)acetyl, (2,6-dimethylphenoxy)acetyl or 2,4,6-dimethylphenoxy)acetyl; B is absent; $R^1$ is hydrogen; and $R^2$ and Y are as defined in the last instance; or a therapeutically acceptable acid addition salt thereof.

Preferably, with reference to the compounds of formula 1 in which B is the divalent radical —$NHCHR^5C(O)$—, the asymmetric carbon atom bearing $R^5$ has the (S) configuration.

Included within the scope of this invention is a pharmaceutical composition for treating HIV infections in a human comprising a compound of formula 1, or a therapeutically acceptable salt thereof, and a pharmaceutically acceptable carrier.

The scope of the invention includes as well a method for treating HIV infections in a human comprising administering thereto an effective amount of the compound of formula 1, or a therapeutically acceptable salt thereof.

Also included within the scope is a method for protecting human cells against HIV pathogenesis comprising treating said cells with an anti-HIV effective amount of a compound of formula 1, or a therapeutically acceptable salt thereof.

Processes for preparing the compounds of formula 1 are described hereinafter.

DETAILS OF THE INVENTION

GENERAL

In general, the abbreviations used herein for designating the amino acids and the protective groups are based on recommendations of the IUPAC-IUB Commission of Biochemical Nomenclature, see European Journal of Biochemistry 138, 9 (1984). For instance, Val, Ile, Thr, Asn, and Leu represent the residues of L-valine, L-isoleucine, L-threonine, L-asparagine and L-leucine, respectively.

The term "lower alkyl" as used herein, either alone or in combination with a radical, means straight chain alkyl radicals containing one to six carbon atoms and branched chain alkyl radicals containing three to four carbon atoms and includes methyl, ethyl, propyl, butyl, hexyl, 1-methylethyl, 1-methylpropyl, 2-methylpropyl and 1,1-dimethylethyl.

The term "lower cycloalkyl" as used herein, either alone or in combination with a radical, means saturated cyclic hydrocarbon radical containing from three to six carbon atoms and includes cyclopropyl, cyclobutyl, cyclopentyl and cyclohexyl.

The term "lower alkoxy" as used herein means straight chain alkoxy radical containing one to six carbon atoms and branched chain alkoxy radicals containing three to four carbon atoms and includes methoxy, ethoxy, propoxy, hexoxy, 1-methylethoxy, butoxy and 1,1-dimethylethoxy. The latter radical is known commonly as tertiary-butyloxy.

The term "halo" as used herein means a halo radical selected from bromo, chloro, fluoro or iodo.

The term "residue" with reference to an amino acid means a radical derived from the corresponding α-amino acid by eliminating the hydroxyl of the carboxy group and one hydrogen of the α-amino group.

The term "tert-butylglycyl" represents the amino acid residue of 2(S)-amino-3,3-dimethylbutanoic acid and the term "$N^4$-methylasparaginyl" represents the amino acid residue of 2(S)-amino-4-methylamino-4-oxobutanoic acid.

The term "Het" as used herein means a monovalent radical derived by removal of a hydrogen from a five- or six-membered saturated or unsaturated heterocycle containing from one to two heteroatoms selected from nitrogen, oxygen and sulfur. Optionally, the heterocycle may bear one or two substituents; for example, lower alkyl, lower alkoxy, halo, amino or lower alkylamino. Examples of suitable heterocylces and optionally substituted heterocycles include pyrrolidine, tetrahydrofuran, thiazolidine, pyrrole, 1H-imidazole, 1-methyl-1H-imidazole, isoxazole, thiazole, 2-methylthiazole, 2-aminothiazole, piperidine, 1,4-dioxane, 4-morpholine, pyridine, 2-methylpyridine, pyrimidine, 4-methylpyrimidine and 2,4-dimethylpyrimidine.

The term "pharmaceutically acceptable carrier" as used herein means a non-toxic, generally inert vehicle for the active ingredient, which does not adversely affect the ingredient.

The term "effective amount" as used herein means a predetermined amount of the compound of this invention sufficient to be effective against HIV in vivo.

PROCESS

In general, the compounds of formula 1 are prepared by known methods using reaction conditions which are known to be suitable for the reactants. Description of the methods are found in standard textbooks such as "Annual Reports In Organic Synthesis—1990", K. Turnbull et al., Eds, Academic Press, Inc., San Diego, Calif., USA, 1990 (and the preceding annual reports), "Vogel's Textbook Of Practical Organic Chemistry", B. S. Furniss et al., Eds, Longman Group Limited, Essex, UK, 1986, and "The Peptides: Analysis, Synthesis, Biology", E. Grass et al., Eds, Academic Press, New York, N.Y., USA, 1979–1987, Volumes 1 to 9.

More particularly, the compounds of formula 1 can be prepared by a process comprising:

(a) reacting an epoxide of formula 2

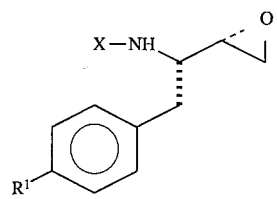

wherein X and $R^1$ are as defined herein with a piperidinecarboxamide of formula 3

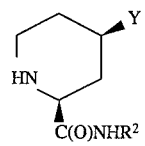

wherein $R^2$ and Y are as defined herein to obtain the corresponding compound of formula 1 wherein X, $R^1$, $R^2$ and Y are as defined herein and B is absent; or (b) reacting a compound of formula 4

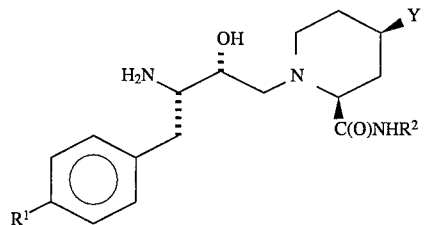

wherein $R^1$, $R^2$ and Y are as defined herein with a reactive derivative of the carboxylic acid X—OH wherein X is $R^3C(O)$ or $R^{3A}OCH_2C(O)$ as defined herein to obtain the corresponding compound of formula 1 wherein X is $R^3C(O)$ or $R^{3A}OCH_2C(O)$ as defined herein, $R^1$, $R^2$ and Y are as defined herein and B is absent; or (c) coupling the compound of formula 4 wherein $R^1$, $R^2$ and Y are as defined herein with an α-amino acid of the formula X-NHCHR$^5$COOH wherein X and $R^5$ are as defined herein in the presence of a coupling agent to obtain the corresponding compound of formula 1 wherein X, $R^1$, $R^2$ and Y are as defined herein and B is the divalent radical —NHCHR$^5$C(O)— wherein $R^5$ is as defined herein; or (d) reacting a compound of formula 5

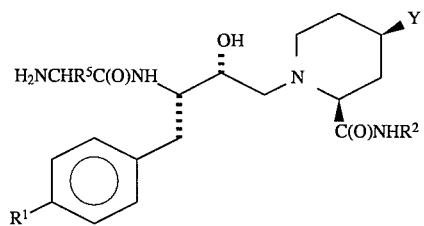

wherein $R^1$, $R^2$, $R^5$ and Y are as defined herein with a reactive derivative of the carboxylic acid X—OH wherein X is $R^3C(O)$ or $R^{3A}OCH_2C(O)$ as defined herein to obtain the corresponding compound of formula 1 wherein X is $R^3C(O)$ or $R^{3A}OCH_2C(O)$ as defined herein, $R^1$ $R^2$ and Y are as defined herein and B is the divalent radical —NHCHR$^5$C(O)— wherein $R^5$ is as defined herein; and (e) if desired, transforming the compound of formula 1, as obtained in the preceding sections (a), (b), (c) or (d), into a corresponding therapeutically acceptable acid addition salt.

It should be noted that the species of compounds of formula 1 in which X is a commonly used N-protective group, e.g. Boc, Z, Fmoc or p-methoxybenzyloxycarbonyl, are obtained most readily and conveniently by processes (a) and (c). The ready accessibility of this species renders them useful as intermediates for a preferred route, via respective processes (b) and (d), to produce the respective compounds of formula 1 in which X is other than a commonly used N-protective group. As intermediates, therefore, the compounds of formula 1 of this species are deprotected (i.e. the protective group is removed), and the resulting N-terminal free amines are used as the respective compounds of formula 4 or formula 5 according to processes (b) and (d), depending on whether B is absent or present, for the ultimate preparation of the compounds of formula 1 in which X is other than a commonly used N-protective group, e.g. 2-pyridinylmethoxycarbonyl or 2-quinolinylcarbonyl.

More explicitly, according to the preceding process (a), the compounds of formula 1 in which B is absent can be prepared by an N-alkylation reaction involving the addition of the epoxide 2 to the piperidinecarboxamide 3. The reaction can be effected conveniently by bringing the two reactants into contact in an inert solvent, e.g. ethanol, tetrahydrofuran or dimethylformamide, at temperatures ranging from 20° to 110° C. The reaction time is dependent on temperature and the nature of the reactants but generally ranges from two to 24 hours.

According to process (b), the compounds of formula 1 in which B is absent are obtained by reacting the corresponding compound of formula 4 with a reactive derivative of the carboxylic acid X—OH. Suitable reactive derivatives are the acylating agents capable of providing the appropriate acyl radical X—CO and include the corresponding acid halides, preferably the chlorides or bromides, active esters, anhydrides or mixed anhydrides. The reaction is performed according to known methods and conditions for accomplishing the reaction including the means to impart the desired selectivity to the reaction by choosing appropriate ratios of the reactants or by temporarily providing known protecting groups, if required, for any other reactive group competing with the intended reactive groups. Generally, the reaction is performed in an inert solvent, e.g. tetrahydrofuran, dimethylformamide or methylene dichloride, at a temperature between 0° and 50° C and a reaction time ranging from 15 minutes to 24 hours.

According to process (c), the compounds of formula 1 in which B is the divalent radical —NHCHR$^5$C(O)— wherein R$^5$ is as defined herein can be obtained by coupling the compound of formula 4 with an α-amino acid of formula X—NHCHR$^5$COOH in the presence of a coupling agent. The use of coupling agents to promote the dehydrative coupling of a free carboxyl of one reactant with a free amino group of the other reactant is well known; for example, see "The Peptides: Analysis, Synthesis, Biology", Volumes 1 to 8, noted hereinbefore. Examples of suitable coupling agents are 1,1'-carbonyldiimidazole or N,N'-dicyclohexyl-carbodiimide. Other examples are 1-hydroxybenzotriazole in the presence of N,N'-dicyclohexylcarbodiimide or N-ethyl-N'-[(3-dimethyl-amino)propyl]carbodiimide. A very practical and useful coupling agent is the commercially available (benzotriazol-1-yloxy)tris(dimethylamino)phosphonium hexafluorophosphate, either by itself or in the presence of 1-hydroxybenzotriazole. Still another very practical and useful coupling agent is the commercially available 2-(1H-benzotriazol-1-yl)-N,N,N',N'-tetramethyluronium tetrafluoroborate.

The coupling reaction is conducted in an inert solvent, e.g. methylene dichloride, acetonitrile or dimethylformamide. An excess of an organic amine, e.g. diisopropylethylamine or N-methylmorpholine, is added to maintain the reaction mixture at a pH of about eight. The reaction temperature usually ranges from −20° to about 30° C. and reaction time from 15 minutes to eight hours.

With reference to process (d), this process is performed in the same manner as described hereinabove for process (b), the only exception being in the use of the compound of formula 5 instead of the compound of formula 4 as a starting material.

The epoxides of formula 2 used as starting materials for the process (a) are either known or can be prepared by known methods. More specifically the epoxides of formula 2 are either described by B. K. Handa et al., European patent application 346,847, published Dec. 20, 1989, or they can be made by methods described in the patent application.

The other starting materials for the processes, i.e. the piperidinecarboxamides of formula 3, and the compounds of formulae 4 and 5, are novel and therefore are an object of this invention. Suitable processes for the preparation of the compounds of formulae 4 and 5 have been noted hereinbefore. The third species of novel intermediates, the piperidinecarboxamides of formula 3, can be prepared by choosing the appropriate 4-substituted piperidine, many of which are known or can be prepared by analogous methods used for preparing the known 4-substituted piperidines, and subjecting the chosen piperidine to known methods for introducing a carboxamide function at position 2 of a piperidine. A convenient method for effecting the latter transformation is illustrated hereinafter in the examples.

The compound of formula 1 of this invention can be obtained in the form of a therapeutically acceptable acid addition salt. Examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 45, 1849 (1960).

In general, the therapeutically acceptable salts of the peptides of formula 1 are biologically fully equivalent to the peptides themselves.

BIOLOGICAL ASPECTS

The HIV protease inhibiting properties and the cell protective effect against HIV pathogenesis of the compounds of formula 1, or a therapeutically acceptable salt thereof, can be demonstrated by biochemical, microbiological and biological procedures.

A particular useful procedure for demonstrating the HIV protease inhibiting properties of the compounds of formula 1 or their therapeutically acceptable salts is the "Recombinant HIV Protease HPLC Assay". The procedure is based on the capacity of the test compound to inhibit enzymatic cleavage by HIV protease of a decapeptide (the substrate) having an amino acid sequence which includes a known HIV protease cleavage site of a HIV polyprotein; see H. G. Krausslich et al., Proc. Natl. Acad. Sci. USA, 86, 807 (1989). Details of this assay together with the results obtained for exemplified compounds of formula 1 are described in the examples hereinafter.

The capacity of the compounds of formula 1 or their therapeutically acceptable salts to protect cells against HIV infection can be demonstrated by microbiological procedures for evaluating the inhibitory effect of a test compound on the cytopathogenicity of HIV in human T4 cell lines. Typical of such procedures are those described by S. Harada and N. Yamamoto, Jpn. J. Cancer Res. (Gann), 76, 432 (1985), and S. Harada et al., Science, 229, 563 (1985). An assay based on the latter procedures is described in the examples hereinafter.

When a compound of this invention, or a therapeutically acceptable salt thereof, is used to combat HIV infections in a human, the peptide can be administered orally, topically or parenterally, in a vehicle comprising one or more pharmaceutically acceptable carriers, the proportion of which is determined by the solubility and chemical nature of the compound, the chosen route of administration and standard biological practice. For oral administration, the compound or a therapeutically acceptable salt thereof can be formulated in unit dosage forms such as capsules or tablets each containing a predetermined amount of the active ingredient, ranging from about 5 to 150 mg, in a pharmaceutically acceptable carrier. For topical administration, the compound can be formulated in a pharmaceutically acceptable vehicle containing 0.01 to 2 percent, preferably 0.05 to 1 percent, of the active agent. Such formulations can be in the form of a cream, lotion, sublingual tablet, or preferably a transdermal patch or buccal patch. For parenteral administration, the compound of formula 1 is administered by either intravenous, subcutaneous or intramuscular injection, in compositions with pharmaceutically acceptable vehicles or carriers. For administration by injection, it is preferred to use the compound in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations can be found in standard pharmaceutical texts, e.g in "Remington's Pharmaceutical Sciences", 18th ed., Mack Publishing Company, Easton, Pa., 1990.

The dosage of the compound will vary with the form of administration and the particular active agent chosen. Furthermore, it will vary with the particular host under treatment. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

For oral administration, the compound or a therapeutically acceptable salt is administered in the range of 0.5 to 15 mg per kilogram of body weight per day, with a preferred range of 0.5 to 5 mg per kilogram. With reference to systemic administration, the compound of formula 1 is administered at a dosage of 1 μg to 100 μg per kilogram of body weight per day, although the aforementioned variations will occur.

Although the formulations disclosed hereinabove are effective and relatively safe medications for treating HIV infections, the possible concurrent administration of these formulations with other antiviral medications or agents to obtain beneficial results is not excluded. Such other antiviral medications or agents include soluble CD4, zidovudine, didanosine, zalcitabine, trisodium phosphonoformate, ribavarin, acyclovir or antiviral interferons (e.g. α-interferon or interleukin-2).

The following examples illustrate further this invention. Solution percentages or ratios express a volume to volume relationship, unless stated otherwise. Temperatures are given in degrees Celsius. Proton nuclear magnetic resonance (NMR) spectra were recorded on a Bruker 200 MHz spectrometer; the chemical shifts (δ) are reported in parts per million. Abbreviations used in the examples include Boc: tert-butyloxycarbonyl; BOP: (benzotri-azol-1-yloxy)tris-(dimethylamino)-phosphonium hexafluorophosphate; $Bu^t$: tert-butyl; Bzl: benzyl; DIEA: diisopropylethylamine; DMF: dimethylformamide; HEPES: N-2-hydroxyethylpiperazine-N'-2-ethanesulfonic acid; $Et_2O$: diethyl ether; EtOAc: ethyl acetate; EtOH: ethanol; HPLC: high performance liquid chromatography; MeOH: methanol; Ph: phenyl;, THF: tetrahydrofuran; Z: benzyloxycarbonyl.

EXAMPLE 1

Preparation of 1-(tert-Butyloxycarbonyl)-4-(phenylthio)piperidine

A solution of 1-(tert-butyloxycarbonyl)-4-piperidinol (3.0 g, 14.9 mmol) in THF (30 mL) was cooled to 0°. Triethylamine (3.2 mL, 1.5 equiv.) was added to the solution, followed by the gradual addition of methylsulfonyl chloride (1.26 mL, 1.1 equiv.). The reaction mixture was stirred at 0° for 2 h. $Et_2O$ (30 mL) and $H_2O$ (20 mL) were added and the mixture was stirred at 0° for an additional 30 min. The mixture was diluted with $Et_2O$ (200 mL). The organic layer was washed successively with $H_2O$, 10% aqueous citric acid, a saturated aqueous solution of $NaHCO_3$ (2×) and brine. The organic layer was dried ($MgSO_4$) and concentrated under reduced pressure to give 1-(tert-butyloxycarbonyl)-4-piperidinol methylsulfonate ester (4.0 g, 96%) as a yellowish solid. $^1H$ NMR ($CDCl_3$) δ4.90 (m, 1H), 3.72 (ddd, J=4.3, 6.5, 13.5 Hz, 2H), 3.32 (ddd, J=4.3, 8.1, 13.5 Hz, 2H), 3.05 (s, 3H), 1.47 (s, 9H).

The latter methylsulfonate was used without further purification to prepare the title compound as follows: Thiophenol (1.84 mL, 17.9 mmol) was added slowly to a suspension of NaH (334 mg, 14.3 mmol) in DMF (8 mL) at 0°. The mixture was stirred for 20 min. A solution of the latter methylsulfonate (2.0 g, 7.17 mmol) in DMF (6 mL) was added and the resultant mixture was stirred at room temperature (20°–22°) for 18 h. The mixture was diluted with $Et_2O$ and the organic phase was washed successively with 1M aqueous NaOH (3×) and brine. The organic layer was dried ($MgSO_4$) and concentrated to dryness under reduced pressure. The residue was purified by flash chromatography ($SiO_2$, eluent: EtOAc-hexane, 1:9 and then 1:6) to give the title compound (1.82 g, 86%) as an oil which solidified on standing. $^1H$ NMR ($CDCl_3$) δ7.48–7.2 (2 m, 2H+3H), 3.97 (m, 2H), 3.22 (m, 1H), 2.80 (ddd, J=3.8, 10.5, 13.5 Hz, 2H), 1.47 (s, 9H). FAB mass spectrum, m/z: 294 $(M+H)^+$.

EXAMPLE 2

Preparation of d,1-cis-N-tert-Butyl-1-(tert-butyloxycarbonyl)-4-(phenylthio)piperidine-2-carboxamide A solution of the title compound of example 1 (3.57 g, 12.2 mmol) in $Et_2O$ (60 mL) was cooled to −78°. N,N,N', N'-Tetramethylenediamine (4.6 mL, 2.5 equiv.) was added to the cooled solution, followed by the gradual addition of 1.3M sec-butyllithium in cyclohexane (12.0 mL, 1.3 equiv.). The mixture was stirred for 3.5 h at −78°. Thereafter, tert-butylisocyanate (2.1 mL, 1.5 equiv.) was added rapidly and the reaction mixture was stirred for 40 min at −78°. The reaction mixture was quenched with 10% aqueous citric acid and then allowed to warm to room temperature. The organic phase was separated and the aqueous phase was extracted with $Et_2O$. The combined organic phases were washed with a saturated aqueous solution of NaHCO₃ and brine, dried (MgSO₄) and evaporated under reduced pressure. The residue was purified by flash chromatography (SiO₂, eluent: hexane-EtOAc, 6:1 and then 4:1) to give the title compound (4.34 g, 90%) as a colorless oil which solidified on standing. $^1$H NMR (CDCl₃) δ7.42 (m, 2H), 7.28 (m, 3H), 5.85 (broad s, 1H), 4.43 (dd, J=4.0, 7.0 Hz, 1H), 3.92 (ddd, J=3.5, 5.0, 13.5 Hz, 1H), 3.49 (m, 1H), 3.32 (ddd, J=4.0, 11.5, 13.5 Hz, 1H), 1.48 (s, 9H), 1.39 (s, 9H). FAB mass spectrum, m/z: 393 (M+H)$^+$.

EXAMPLE b 3

Preparation of d,1-cis-N-tert-Butyl-1-(tert-butyloxycarbonyl)-4-(2-pyridinyloxy)piperidine-2-carboxamide A solution of 1-(tert-butyloxycarbonyl)-4-piperidinol (5.2 g, 25.9 mmol), tert-butyldimethylsilyl chloride (4.07 g, 1.05 equiv.) and imidazole (2.7 g, 1.5 equiv.) in DMF (20 mL) was stirred for 16 h. After dilution with Et₂O, the solution was washed successively with H₂O (2×), 10% aqueous citric acid, a saturated aqueous solution of NaHCO₃ and brine. The organic layer was dried (MgSO₄) and concentrated to dryness. The residue was purified by HPLC using a WATERS® LC-500 preparative chromatography apparatus [2 SiO₂ columns: hexane-EtOAc (19:1), Millipore Corporation, Milford, Mass., USA] to give 1-(tert-butyloxycarbonyl)-4-(tert-butyldimethylsiloxy)piperidine (7.54 g, 92%). $^1$H NMR (CDCl₃) δ3.87 (m, 1H), 3.61 (ddd, J=3.5, 7.5, 13.0 Hz, 2H), 3.24 (ddd, J=3.7, 8.0, 13.0 Hz, 2H), 1.48 (s, 9H), 0.88 (s, 9H), 0.07 (s, 6H).

Thereafter, by following the procedure of example 2 but replacing 1-(tert-butyloxycarbonyl)-4-(phenylthio)piperidine with the aforementioned 1-(tert-butyloxycarbonyl)-4-(tert-butyldimethylsiloxy)piperidine, d,1-cis-N-tert-butyl-1-(tert-butyloxycarbonyl)-4-(tert-butyldimethylsiloxy)piperidine-2-carboxamide was obtained. $^1$H NMR (CDCl₃) δ5.70 (s, 1H), 4.47 (dd, J=2.7, 8.0 Hz, 1H), 4.07 (m, 1H), 3.83 (m, 1H), 3.22 (ddd, J=5.4, 10.5, 13.5 Hz), 1.48 (s, 9H), 1.35 (s, 9H), 0.88 (s, 9H), 0.1 and 0.08 (2 s, 6H).

To a solution of the latter compound (700 mg, 1.69 mmol) in THF (10 mL), a solution of 1M tetrabutylammonium fluoride in THF (2.15 mL, 1.25 equiv.) was added. The reaction mixture was stirred at room temperature for 30 min and then diluted with Et₂O. The resultant mixture was washed with H₂O (2×) and brine (1×). The organic layer was dried (MgSO₄) and concentrated to dryness under reduced pressure. The residue was purified by flash chromatography (SiO₂, eluent: hexane-EtOAc, 1:1) to give the carboxamide, d,1-cis-N-tert-butyl-1-(tert-butyloxycarbonyl)-4-hydroxypiperidine-2-carboxamide (386 mg, 76%), as a white solid. FAB mass spectrum, m/z: 301 (M+H)$^+$.

Diethyl azodicarboxylate (173 μL, 1.5 equiv.) was added to a cold solution (0°) of the latter carboxamide (220 mg, 0.73 mmol), 4-nitrobenzoic acid (244 mg, 2.0 equiv.) and triphenylphosphine (288 mg, 1.5 equiv.) in benzene-THF (5:1, 13 mL). The reaction mixture was stirred at 0° for 30 min and then at room temperature for 3 h. The solvent was removed under reduced pressure. The residue was purified by flash chromatography (SiO₂, eluent: hexane-EtOAC, 4:1) to give d,1-trans-N-tert-butyl-1-(butyloxycarbonyl)-4-(4-nitrobenzoyloxy)-2-carboxamide (280 mg) containing about 25 to 30% of a contaminant (an elimination product). The total product was used for the next step without further purification.

A mixture of the latter product (404 mg, 0.9 mmol) and K₂CO₃ (28 mg, 0.2 equiv.) in MeOH (9 mL) was stirred at room temperature for 18 h. The solvent was removed under reduced pressure. The residue was dissolved in CHCl₃ and the resulting solution was washed with H₂O, dried (MgSO₄) and concentrated to dryness under reduced pressure. The residue was purified by flash chromatography (SiO₂, eluent: hexane-EtOAc, 1:1 and then 1:2) to give d,1-trans-tert-butyl-1-(N-tert-butyloxycarbonyl)-4-hydroxypiperidine-2-carboxamide (194 mg, 71%).

A solution of the latter compound (145 mg, 0.48 mmol), 2-hydroxypyridine (68 mg, 1.5 equiv.) and triphenylphosphine (187 mg, 1.5 equiv.) in benzene-THF (5:1, 12 mL) was cooled to 0°. Diethyl azodicarboxylate (114 μL, 1.5 equiv.) was added to the solution. The mixture was stirred for 1.5 h at 0° and then at room temperature for 30 min. The solvent was removed under reduced pressure. The residue was purified by flash chromatography (SiO₂, eluent: hexane-EtOAc, 2:1) to give the title compound of this example (70 mg, 38%). $^1$H NMR (CDCl₃) δ8.12, 7.43, 6.85 and 6.62 (4 m, 4H), 5.72 (s, 1H), 5.39 (m, 1H), 4.63 (m, 1H), 4.05 (m, 1H), 3.29 (m, 1H), 1.48 (s, 9H), 1.36 (s, 9H).

EXAMPLE 4

Preparation of d,1-cis-N-tert-Butyl-1-(tert-butyloxycarbonyl)-4-(phenylsulfonyl)piperidine-2-carboxamide A mixture of the title compound of example 2 (1.68 g, 4.28 mmol) and 3-chloroperoxybenzoic acid (2.2 g, 12.83 mmol) in CH₂Cl₂ (20 mL) was stirred at room temperature for 18 h. The reaction mixture was quenched with a 10% aqueous solution of sodium sulfite and then diluted with EtOAc. The organic layer was separated, washed successively with a saturated aqueous solution of NaHCO₃, H₂O and brine, dried (MgSO₄) and concentrated under reduced pressure. The solid residue was triturated with hexane-EtOAc (18 mL/12 mL) and then collected on a filter to give the title compound (1.57 g, 86%) as a white solid. $^1$H NMR(CDCl₃) δ7.90 (m, 2H), 7.75–7.55 (m, 3H), 5.95 (s, 1H), 4.07 (dd, J=8.0, 9.5 Hz, 1H), 3.88 (dt, J=5.4, 13.5 Hz, 1H), 3.32–3.05 (m, 2H), 1.45 (s, 9H), 1.35 (s, 9H). FAB mass spectrum, m/z: 425 (M+H)$^+$.

By the following the procedure of this example, but using only one molar equivalent of 3-chloroperoxybenzoic acid, d,1-cis-N-tert-butyl-1-(tert-butyloxycarbonyl)-4-(phenylsulfinyl)piperidine-2-carboxamide was obtained.

EXAMPLE 5

Preparation of N-tert-Butyl-1-[3(S)-(tert-butyloxycarbonylamino)-2(R)-hydroxy-4-phenylbutyl]-4(R)-(phenylthio)piperidine-2(S)-carboxamide (formula 1: X=Boc, B is absent, R¹=H, R²=C(CH₃)₃ and Y=PhS)

(a) d,1-cis-N-tert-Butyl-4-(phenylthio)piperidine-2-carboxamide, a piperidinecarboxamide of formula 3 in which R² is C(CH₃)₃ and Y is PhS, was prepared as follows: A solution of the corresponding Boc-protected derivative of the piperidinecarboxamide (3.04 g, 7.76 mmol), i.e. the title compound of example 2, in 6N HCl dioxane was stirred at room temperature for 20 min and then concentrated to dryness under reduced pressure to give the desired piperidinecarboxamide of formula 3 wherein R² is C(CH₃)₃ and Y is PhS.

(b) The title compound of this example was prepared as follows: A mixture of the latter piperidinecarboxamide in EtOAc (50 mL) and 2N aqueous NaOH (20 mL) was stirred at room temperature for 15 min. The organic layer was separated, washed with a minimum amount of H₂O and brine, dried (MgSO₄) and evaporated to dryness under reduced pressure. The resulting oil was dried under high vacuum for about 45 min. The oil was mixed with the epoxide of formula 2, 3(S)-(tert-butyloxycarbonylamino)-1,2(R)epoxy-4-phenylbutane (2.45 g, 9.36 mmol), see B. K. Handa et al., supra, and absolute EtOH (40 mL). The mixture was heated at reflux for 18 h. After an additional amount of the epoxide (600 mg) was added, the mixture was heated at reflux for 4 h. The mixture was concentrated to dryness under reduced pressure. The crude product was purified by HPLC using a WATERS® LC-500 preparative chromatography apparatus [2 $SiO_2$ columns: hexane-EtOAc (6:4), Millipore Corporation, Milford, Mass., USA] to give the title compound as a white foam [1.46 g, 34% for the desired (more polar) isomer]. FAB mass spectrum, m/z: 556 $(M+H)^+$.

The procedure of example 5 may be followed to prepare other compounds of formula 1 in which B is absent and X, $R^1$, $R^2$ and Y are as defined herein. For example, by replacing 3(S)-(tert-butyloxycarbonylamino)-1,2(R)-epoxy-4-phenylbutane with an equivalent amount of 3(S)-(tert-butyloxycarbonylamino)-1,2(R)-epoxy-4-(4-fluorophenyl)butane, N-tert-butyl-1-{3(S)-{(benzyloxycarbonyl)amino}-2(R)-hydroxy-4-(4-fluorophenyl)butyl}-4(R)-(phenylthio)piperidine-2(S)-carboxamide [FAB mass spectrum, m/z: 608 $(M+H)^+$] is obtained.

Still other examples of such compounds are listed in Table I. In each of these examples an equivalent amount of the epoxide of formula 2 listed therein is used instead of the epoxide of formula 2 described in example 5 and an equivalent amount of the piperidinecarboxamide of formula 3 listed therein instead of the piperidinecarboxamide of formula 3 described in example 5.

TABLE I

| Entry No. | Epoxide of Formula 2 | | Piperidine-carboxamide of Formula 3 | | Product: N-tert-Butyl-1-{3(S)-{(X)-amino}-2(R)-hydroxy-4-phenyl-butyl}-Y-piperidine-2(S)-carboxamide |
|---|---|---|---|---|---|
| | X | $R^1$ | $R^2$ | Y | X//Y |
| 1 | Z | H | $Bu^t$ | Ph | benzyloxycarbonyl//4(R)-phenyl (558)* |
| 2 | Z | H | $Bu^t$ | Bzl | benzyloxycarbonyl//4(R)-benzyl (572) |
| 3 | Z | H | $Bu^t$ | $SO_2Ph$ | benzyloxycarbonyl//4(R)-(phenylsulfonyl) (622) |
| 4 | Z | H | $Bu^t$ | SPh | benzyloxycarbonyl//4(R)-(phenylthio) (590) |
| 5 | Z | H | $Bu^t$ | OPh | benzyloxycarbonyl//4(R)-phenoxy (574) |
| 6 | Z | H | $Bu^t$ | O-(2-pyridyl) | benzyloxycarbonyl//4(R)-(2-pyridinyloxy) (575) |
| 7 | Z | H | $Bu^t$ | cyclohexyl | benzyloxycarbonyl//4(R)-cyclohexyl(564) |
| 8 | Z | H | $Bu^t$ | S-(2-pyridinyl) | benzyloxycarbonyl//4(R)-(2-pyridinylthio) (591) |
| 9 | Z | H | $Bu^t$ | S-(4-pyridinyl) | benzyloxycarbonyl//4(R)-(4-pyridinylthio) (591) |
| 10 | Z | H | $Bu^t$ | S-(2-pyrimidinyl) | benzyloxycarbonyl//4(R)-(2-pyrimidinylthio) (592) |
| 11 | Z | H | $Bu^t$ | S-(4,6-dimethyl-2-pyrimidinyl) | benzyloxycarbonyl//4(R)-(4,6-dimethyl-2-pyrimidinylthio) (620) |
| 12 | Z | H | $Bu^t$ | $SCH_2Ph$ | benzyloxycarbonyl//4(R)-benzylthio (604) |
| 13 | Z | H | $Bu^t$ | S-(4-pyridinyl-methyl) | benzyloxycarbonyl//4(R)-{(4-pyridinylmethyl)thio} (605) |
| 14 | Z | H | $Bu^t$ | S-(3-pyridinyl-methyl) | benzyloxycarbonyl//4(R)-{(3-pyridinylmethyl)thio} (605) |
| 15 | Boc | H | $Bu^t$ | O-(2-pyridinyl-methyl) | tert-butyloxycarbonyl//4(R)-(2-pyridinylmethoxy) (555) |
| 16 | Boc | H | $Bu^t$ | S-(2-pyridinyl-methyl) | tert-butyloxycarbonyl//4(R)-{(2-pyridinylmethyl)thio} (571) |
| 17 | Boc | H | $Bu^t$ | O-(2-pyrimidinyl) | tert-butyloxycarbonyl//4(R)-(2-pyrimidinyloxy) (542) |
| 18 | Boc | H | $Bu^t$ | O-(4,6-dimethyl-2-pyrimidinyl) | tert-butyloxycarbonyl//4(R)-{(4,6-dimethyl-2-pyrimidinyl)oxy} (570) |
| 19 | Boc | H | $Bu^t$ | O-(4-methyl-2-pyrimidinyl) | tert-butyloxycarbonyl//4(R)-{(4-methyl-2-pyrimidinyl)oxy} (556) |
| 20 | Boc | H | $Bu^t$ | O-(2,6-dimethyl 4-pyrimidinyl) | tert-butyloxycarbonyl//4(R)-{(2,6-dimethyl-4-pyrimidinyl)oxy} (570) |
| 21 | Boc | H | $Bu^t$ | S-(2,6-dimethyl 4-pyrimidinyl) | tert-butyloxycarbonyl//4(R)-{(2,6-dimethyl-4-pyrimidinyl)thio} (586) |
| 22 | Boc | H | $Bu^t$ | S-(4-methyl-2-pyrimidinyl) | tert-butyloxycarbonyl//4(R)-{(4-methyl-2-pyrimidinyl)thio} (572) |

*The number in parenthesis following the designation of the product for each entry is the found $(M + H)^+$ from the FAB mass spectrum of the product.

EXAMPLE 6

Two procedures for the preparation of compounds of formula 1 in which B is the divalent radical —NHCHR$_5$C(O)— wherein R$^5$ is as defined herein are provided in this example. The first exemplified procedure, example 6A, is preferred for compounds of formula 1 in which B is other than Asn, and the second exemplified procedure, example 6B, is preferred for compounds of formula 1 in which B is Asn.

A: Preparation of N-tert-Butyl-1-{3(S)-{{N-(tert-butyloxycarbonyl)valyl}amino}-2(R)-hydroxy-4-phenylbutyl}-4(R)-(phenylthio)piperidine-2(S)-carboxamide (formula 1; X=Boc, B=Val, R$^1$=H, R$^2$=C(CH$_3$)$_3$ and Y=PhS)

A solution of the compound of formula 1 wherein X is Boc, B is absent, R$^1$=H, R$^2$=C(CH$_3$)$_3$ and Y=PhS (1.14 g, 2.04 mmol), i.e. the title compound of example 5, in 6N HCl/dioxane (10 mL) was stirred at room temperature for 30 min. The solvent was removed under reduced pressure. The white solid residue was triturated with Et$_2$O, collected on a filter and dried to give the corresponding deprotected amine as a hydrochloride salt (1.06 g, 98%).

The latter salt (341 mg, 0.645 mmol) was dissolved in CH$_2$Cl$_2$ (3.5 mL). DIEA (225 μL, 1.29 mmol), the protected amino acid Boc-Val-OH (145 mg, 0.667 mmol) and BOP (342 mg, 0.774 mmol) were added to the solution of the salt. The reaction mixture was maintained at pH 8 by periodic verification and the addition of DIEA as required while the reaction mixture was stirred at room temperature for 3.5 h. Thereafter, the reaction mixture was diluted with EtOAc, washed successively with a saturated aqueous solution of NaHCO$_3$ (2×), H$_2$O and brine. The organic layer was dried (MgSO$_4$) and concentrated under reduced pressure. The residue was purified by flash chromatography (SiO$_2$, eluent: hexane-EtOAc, 1:1) to give the title compound of section A of this example as a white solid (338 mg, 80%). FAB mass spectrum, m/z: 655.3 (M+H)$^+$.

B: Preparation of N-tert-Butyl-1-{3(S)-{{N-(tert-butyloxycarbonyl)asparaginyl}amino}-2(R)-hydroxy-4-phenylbutyl}-4(R)-(phenylthio)piperidine-2(S)carboxamide (formula 1; X=Boc, B=Asn, R$^1$=H, R$^2$=C(CH$_3$)$_3$ and Y=PhS)

1-Hydroxybenzotriazole (1.97 g, 14.57 mmol) was added to a cooled (0°) solution of N,N'-dicyclohexylcarbodiimide (2.4 mmol/mL in CH$_2$Cl$_2$, 6.7 mL, 16.08 mmol) and THF (45 mL). The mixture was stirred for 15 min. The protected amino acid Boc-Asn-OH (3.38 g, 14.57 mmol) and a solution of the corresponding deprotected amine of the title compound of example 5 (3.30 g, 7.24 mmol) in DMF (40 mL) were added to the mixture. (Note: The deprotected amine was obtained as described in the first paragraph of example 6A, followed by transforming the hydrochloride salt to its free base.) The mixture was allowed to warm slowly to room temperature and then stirred for 18 h. Thereafter, the mixture was diluted with EtOAc and H$_2$O. The organic phase was separated, washed with a saturated aqueous solution of NaHCO$_3$, H$_2$O and brine, dried (MgSO$_4$) and concentrated to dryness under reduced pressure. The solid residue was purified by flash chromatography (SiO$_2$, eluent: CHCl$_3$-MeOH, 97.5:2.5) to give the title compound of section B of this example as a white solid (3.56 g, 73%). FAB mass spectrum, m/z: 670 (M+H)$^+$.

The procedures of example 6 may be followed to prepare other compounds of formula 1 in which B is the divalent radical —NHCHR$^5$C(O)— wherein R$^5$ is as defined herein and R$^1$, R$^2$, X and Y are as defined herein. For example, with reference to section A of this example, by replacing the title compound of example 5 with an equivalent amount of N-tert-butyl-1-{3(S)-{(benzyloxycarbonyl)amino}-2(R)-hydroxy-4(4-fluorophenyl)butyl}-4(R)-(phenylthio)piperidine-2(S)-carboxamide, described in example 5, N-tert-butyl-1-{3(S)-{{N-(benzyloxycarbonyl)valyl}amino}-2(R)-hydroxy-4-(4-fluorophenyl)butyl}-4(R)-(phenylthio)piperidine-2(S)-carboxamide {Mass spectrum, m/z: 707 (M+H)$^+$} is obtained.

Still other examples of such compounds are listed in Table II. In each of these examples an equivalent amount of the starting material of formula 1 wherein B is absent, listed therein, is used (if different) instead of the compound of formula 1 in which B is absent described in example 6; and an equivalent amount of the protected amino acid of formula PG-AA-OH wherein PG is an α-amino protective group and AA is an amino acid residue of formula NHCHR$^5$C(O) wherein R$^5$ is as defined herein, as listed in Table II, instead of the protected amino acid described in example 6.

TABLE II

| Entry No. | Entry No. of Starting Material of Formula 1 in Table I of Example 6 | Protected Amino Acid Of Formula PG-AA-OH | | Product: N-tert-Butyl-1-{3(S)-{{N-PG-AA}amino}-2(R)-hydroxy-4-phenyl-butyl}-Y-piperidine-2(S)-carboxamide PG-AA//Y |
|---|---|---|---|---|
| | | PG | AA | |
| 1 | 1 | Z | Val | (benzyloxycarbonyl)-valyl//4(R)-(phenylthio) (689)* |
| 2 | 1 | Z | Asn | (benzylocarbonyl)-asparaginyl//4(R)-(phenylthio) (704.3) |
| 3 | 1 | Boc | Asn | (tert-butyloxycarbonyl)asparaginyl//4(R)-(phenylthio) (670) |
| 4 | 2 | Z | Val | (benzyloxycarbonyl)-valyl//4(R)-phenyl (657) |
| 5 | 2 | Z | Ile | (benzyloxycarbonyl)-isoleucyl//4(R)-phenyl (671) |
| 6 | 2 | Z | Asn | (benzyloxycarbonyl)-asparaginyl//4(R)-phenyl (672) |
| 7 | 3 | Z | Val | (benzyloxycarbonyl)-valyl//4(R)-benzyl (671) |
| 8 | 4 | Z | Val | (benzyloxycarbonyl)-valyl//4(R)-(phenyl-sulfonyl) (721) |
| 9 | 4 | Z | Asn | (benzyloxycarbonyl)-asparaginyl//4(R)-(phenylsulfonyl) (736) |
| 10 | 5 | Z | Val | (benzyloxycarbonyl)-valyl//4(R)-phenoxy (673) |
| 11 | 5 | Z | Asn | (benzyloxycarbonyl)-asparaginyl//4(R)-phenoxy (688) |
| 12 | 6 | Z | Val | (benzyloxycarbonyl)-valyl//4(R)-(2-pyridinyloxy) (674) |
| 13 | 7 | Z | Val | (benzyloxycarbonyl)-valyl//4(R)-cyclohexyl (663) |
| 14 | 8 | Z | Val | (benzyloxycarbonyl)-valyl//4(R)-(2-pyridinylthio) (690) |
| 15 | 9 | Z | Val | (benzyloxycarbonyl)-valyl//4(R)-(4-pyridinylthio) (690) |
| 16 | 10 | Z | Val | (benzyloxycarbonyl)-valyl//4(R)-(2-pyrimidinylthio) (691) |
| 17 | 11 | Z | Val | (benzyloxycarbonyl)-valyl//4(R)-{(4,6-dimethyl-2-pyrimidinyl)thio} (719) |

TABLE II-continued

| Entry No. | Entry No. of Starting Material of Formula 1 in Table I of Example 6 | Protected Amino Acid Of Formula PG-AA-OH | | Product: N-tert-Butyl-1-{3(S)-{{N-PG-AA}amino}-2(R)-hydroxy-4-phenyl-butyl}-Y-piperidine-2(S)-carboxamide |
| --- | --- | --- | --- | --- |
| | | PG | AA | PG-AA//Y |
| 18 | 12 | Z | Val | (benzyloxycarbonyl)-valyl//4(R)-(benzyl-thio) (703) |
| 19 | 13 | Z | Val | (benzyloxycarbonyl)-valyl//4(R)-{(4-pyridinylmethyl)thio} (704) |
| 20 | 14 | Z | Val | (benzyloxycarbonyl)-valyl//4(R)-{(3-pyridinylmethyl)thio} (704) |
| 21 | 16 | Z | Val | (benzyloxycarbonyl)-valyl//4(R)-{(2-pyridinylmethyl)thio} (704) |

*The number in parenthesis following the designation of the product for each entry is the found (M + H)⁺ from the FAB mass spectrum of the product.

EXAMPLE 7

Preparation of N-tert-Butyl-1-{2 (R)-hydroxy-4-phenyl-3 (S)-{{N-(2-quinolinylcarbonyl)valyl}amino}butyl}-4(R)-(phenylthio)piperidine-2(S)-carboxamide (formula 1; X=2-quinolinylcarbonyl, B=Val, $R^1$=H, $R^2$=C(CH$_3$)$_3$ and Y=PhS)

A solution of the title compound of section A of example 6 (167 mg, 0.255 mmol) in 6N HCl/dioxane (2.0 mL) was stirred at room temperature for 20 min. The solvent was removed under reduced pressure. The residue, a white solid, was dried under high vacuum for 20 min to give the corresponding deprotected amine as a hydrochloride salt. The latter salt was dissolved in CH$_2$Cl$_2$ (2 mL). DIEA (89 μL, 0.510 mmol), 2-quinolinecarboxylic acid (48.6 mg, 0.280 mmol) and BOP (135 mg, 0.306 mmol) were added to the solution of the salt. The reaction mixture was stirred at room temperature for 3.5 h while the pH of the mixture was maintained at 8 by periodic verification and the addition of DIEA when required. Thereafter, the reaction mixture was diluted with EtOAc and washed successively with a saturated aqueous solution of NaHCO$_3$ (2×), H$_2$O (2×) and brine. The organic layer was dried (MgSO$_4$) and concentrated to dryness under reduced pressure. The resulting colorless oil was purified by flash chromatography (SiO$_2$, eluent: hexane-EtOAc, 2:3) to give the title compound as a white solid (161 mg, 89%). FAB mass spectrum, m/z: 710 (M+H)⁺.

By following the procedure of example 7, or by following the coupling procedure of section B of example 6 in the instance when the starting material is a compound of formula 1 wherein B is Asn, but replacing the title compound of section A of example or the title compound of example 5, respectively, with the appropriate compound of formula 1 wherein B is the divalent radical —NHCHR$_5$C(O)— wherein $R^5$ is as defined herein, X is a commonly used N-protective group, and $R^1$, $R^2$ and Y are as defined herein, and replacing 2-quinolinecarboxylic acid, or the protected amino acid Boc-Asn-OH (in section B of example 6), respectively, with the appropriate carboxylic acid of formula X—OH wherein X is as defined herein, then the following compounds of formula 1 listed in TABLE III, are obtained.

TABLE III

| Entry No. | Product: N-tert-butyl-1-{3(S)-{N-{PG-AA}amino}-2(R)-hydroxy-4-phenylbutyl}-Y-piperidine-2(S)-carboxamide PG-AA//Y |
| --- | --- |
| 1 | (2-quinolinylcarbonyl)asparaginyl//4(R)-phenoxy (709)* |
| 2 | (2-quinolinylcarbonyl)asparaginyl//4(R)-(phenylsulfonyl) (757) |
| 3 | (2-quinolinylcarbonyl)asparaginyl//4(R)-(phenylthio) (725) |
| 4 | (2-naphthalenylcarbonyl)valyl//4(R)-(phenylthio) (709) |
| 5 | (2-naphthalenylcarbonyl)asparaginyl//4(R)-(phenylthio) (724) |

*The number in parenthesis following the designation of the product for each entry is the found (M + H)⁺ from the FAB mass spectrum of the product.

EXAMPLE 8

Preparation of N-tert-Butyl-1-{2 (R)-hydroxy-4-phenyl-3(S)-{{N-{(2-pyridinylmethoxy)carbonyl}isoleucyl}amino}butyl}-4(R)-phenylpiperidine-2(S)carboxamide (formula 1; X=2-pyridinylmethoxycarbonyl, B=Ile, $R^1$=H, $R^2$=C(CH$_3$)$_3$ and Y=Ph)

N-tert-butyl-1-{3(S)-amino-2(R)-hydroxy-4-phenylbutyl}-4(R)-phenylpiperidine-2(S)-carboxamide {prepared by hydrogenolysis (5% Pd/C, 1 atmosphere, MeOH, 2 h) from 0.605 mg (0.108 mmol) of N-tert-butyl-1-{3(S)-(benzyloxycarbonylamino)-2(R)-hydroxy-4-phenylbutyl}-4(R)-phenylpiperidine-2(S)-carboxamide (see entry 1 of Table I)} was dissolved in DMF (1.6 mL). The lithium salt of N-{(2-pyridinylmethoxy)carbonyl}isoleucine (586 mg, 0.228 mmol), 1-hydroxybenzotriazole (32 mg, 0.237 mmol) and N-ethyl-N'-{3-(dimethylamino)propyl}carbodiimide (45.4 mg, 0,237 mmol) were added to the solution. The mixture was stirred at room temperature for 18 h. Thereafter, the reaction mixture was diluted with Et$_2$O, washed with H$_2$O, a saturated aqueous solution of NaHCO$_3$ (2×) and brine, dried (MgSO$_4$) and evaporated to dryness. The resulting yellow oil was purified by flash chromatography (SiO$_2$, eluent: CHCl$_3$, MeOH, 97.5:2.5 and then 95:5) to give the title compound as a white solid (58.7 mg). FAB mass spectrum, m/z: 672 (M+H)⁺.

EXAMPLE 9

Preparation of N-tert-Butyl-1-{2(R)-hydroxy-3(S)-{N-{{N-methyl-N-(2-pyridinylmethyl)amino}carbonyl}valyl}-4-phenylbutyl}-4(R)-(phenylthio)piperidine-2(S)-carboxamide (formula 1; X=$R^3$N$R^4$C(O) wherein $R^3$ =(2-pyridinylmethyl) and $R^4$=CH$_3$, B=Val, $R^1$=H, $R^2$=C(CH$_3$)$_3$ and Y=PhS)

A solution of 1.9M phosgene in toluene (9.41 mL, 17.89 mmol) was added to a suspension of H-Val-OCH$_3$.HCl (1.0 g, 5.96 mmol). The reaction mixture was heated at reflux for 2 h under a dry ice condenser, cooled to room temperature, sparged vigorously with nitrogen for 1.5 h and then concentrated to dryness. Toluene (5 mL) was added to the residue and the resulting solution concentrated to dryness to give (S)-2-isocyanato-3-methylbutanoic acid methyl ester. This product was dried under high vacuum for 5 min and then used in the following step. ¹H NMR(CDCl$_3$) δ3.95–3.94 (d, J=3.82 Hz, 1H), 3.81 (s, 3H), 2.35–2.22 (m, 1H), 1.04–1.02 (d, J=6.8 Hz, 3H), 0.91–0.89 (d, J=6.74 Hz, 3H).

The latter product (471 mg, 3.00 mmol) was dissolved in toluene (5 mL). N-Methyl-N-(2-pyridinylmethyl)amine {366 mg, 3.00 mmol, described by A. Fischer et al., Can. J.

Chem., 56, 3059 (1978)} was added to the solution. The resulting mixture was stirred under $N_2$ at 90° for 16 h. The solvent was evaporated and the residue was purified by flash chromatography ($SiO_2$, eluent: EtOAc-MeOH, 24:1) to yield N-{{N-methyl-N-(2-pyridinylmethyl)amino}carbonyl}valine methyl ester (616 mg, 73%) as an orange oil. $^1$H NMR($CDCl_3$) δ8.58–8.55 (d, 1H), 7.72–7.65 (t, 1H), 7.29–7.19 (m, 2H), 6.20–6.05 (broad s, 1H), 4.55 (s, 2H), 4.45–4.40 (m, 1H), 3.71 (s, 3H), 3.04 (s, 3H), 2.21–2.12 (m, 1H), 1.0–0.92 (dd, 6H).

A solution of 1N LiOH (1.72 mL; 1.72 mmol) was added, via a syringe pump, over a period of 3 h to a vigorously stirred solution of the last named ester (400 mg, 1.43 mmol) in dioxane (4 mL) and $H_2O$ (1 mL) at room temperature. The reaction mixture was stirred at room temperature for 18 h and then evaporated to dryness. The residue was pulverized and dried over $P_2O_5$ under high vacuum to yield the lithium salt of N-{{N-methyl-N-(2-pyridinylmethyl)amino}carbonyl}valine (390 mg; 100%).

The latter lithium salt was coupled with N-tert-butyl-1-{3(S)-amino-2(R)-hydroxy-4-phenylbutyl}-4(R)-(phenylthio)piperidine-2(S)-carboxamide (prepared by the hydrogenolysis of the compound of entry 1 of Table II) according to the coupling procedure of example 8 to give the title compound of this example. FAB mass spectrum, m/z: 703 $(M+H)^+$.

EXAMPLE 10

Preparation of N-tert-Butyl-1-{3(S)-{{(2,6-dimethylphenoxy)acetyl}amino}-2(R)-hydroxy-4-phenylbutyl}-4(R)-{(3-pyridinylmethyl)thio}piperidine-2(S)-carboxamide (formula 1; X=(2,6-dimethylphenoxy)acetyl, B is absent, $R^1$=H, $R^2$=$C(CH_3)_3$ and Y, is (3-pyridinylmethyl)thio)

The corresponding N-Boc derivative of the product described in entry 14, Table I of example 5 was converted to its corresponding primary amine, i.e. N-tert-butyl-1-(3(S)-amino-2(R)-hydroxy-4-phenylbutyl)-4(R)-{(3-pyridinylmethyl)thio}piperidine-2-carboxamide, by removal of the Boc protecting group in the usual manner. The primary amine was isolated in the form of its trishydrochloride salt. The latter compound (154 mg, 0.27 mmol), (2,6-dimethylphenoxy)acetic acid (55.1 mg, 0.31 mmol) and BOP (147 mg, 0.33 mmol) were mixed in anhydrous DMF (4 mL). DIEA (185 μL, 1.06 mmol) was added to the mixture. The mixture was stirred at room temperature for 10 min. Another portion of DIEA (95 μL, 0.55 mmol) was added and the mixture was stirred at the same temperature for 18 h. The reaction mixture was diluted with EtOAc (25 mL), washed successively with a saturated aqueous solution of $NaHCO_3$, $H_2O$ and brine, dried ($MgSO_4$) and concentrated to dryness. The residue was purified by flash chromatography ($SiO_2$, eluent: gradients of 0.1% EtOH/EtOAc to 5% EtOH/EtOAc) to give the title compound as a pale yellow solid (107 mg, 64%); FAB mass spectrum, m/z: 633 $(M+H)^+$.

EXAMPLE 11

Recombinant HIV Protease HPLC Assay:

Enzyme: HIV protease was expressed in *E. coli* {construct pBRT1 prt$^+$, see W. G. Farmerie et al., Science, 236, 305 (1987)}, according to the following protocol:

Unless stated otherwise, all solutions are aqueous solutions.

(i) Fermentation.

*E. coli* cells containing the pBRT1 prt$^+$ plasmid were used to inoculate a seed culture media composed of Luria-Bertani Broth containing 100 μg/mL of ampicillin. Flasks were incubated at 37° under agitation for 17 h. Production flasks containing sterile M9 broth, supplemented with 100 μg/mL of ampicillin, were inoculated at a level of 1% (v/v) using the seed culture described above. Total volume in each production flask was 500 mL in a 2 L Erlenmeyer flask. Flasks were incubated at 37° under agitation until a cell concentration corresponding to an optical density (λ540 μm) of 0.6 was reached (no dilution). This time span was routinely 3–4 h. Flasks were then supplemented with 5 mM isopropylthiogalactoside (IPTG, Research Organics, Cleveland, Ohio, USA) and incubation was continued until the cell concentration reached an optical density of 0.2 at 16-fold dilution. Flasks were then supplemented with 1 mM phenylmethylsulfonyl fluoride (PMSF) and rapidly chilled to 4°. The bacterial cells were recovered by centrifugation at 4°. The wet pellet was stored at −70°.

(ii) Extraction and preparation of Assay Grade Enzyme

All steps below were performed at 4° unless otherwise indicated. Thawed cells were mixed with buffer A {50 mM tris(hydroxymethyl)aminoethane HCl (Tris-HCl, pH 7.4); 0.6 mM ethylenediaminetetraacetic acid (EDTA); 0.375M NaCl, 0.2% Nonidet P-40® (BDH Chemicals Ltd., Poole, UK); 1 mM PMSF}, at a ratio of one part cells to nine parts buffer A. Diatomaceous earth (Celite 545®, John Manville, Lompoc, Calif. USA) was added at a ratio of two parts to one part of wet cell weight. The resulting slurry was homogenized at high speed (ca. 20,000 rpm) on a Waring® industrial blender for 8×15 sec. pulses. Cell debris/Celite® was collected by centrifugation and the resulting pellet was extracted with 4.5 parts of buffer A to one part wet solids using the homogenization procedure described above. Supernatants from both homogenization steps were combined and soluble protein was precipitated by the addition of solid $(NH_4)_2SO_4$ to yield a final concentration of 75% saturation. This mixture was agitated for 60 min and the precipitate was recovered by centrifugation. The resulting pellet was suspended in buffer B {50 mM Tris-HCl, pH 8; 30 mM NaCl; 1 mM DL-dithiothreitol (DTT); 1 mM EDTA; 1 mM PMSF; 10% glycerol}, and dialyzed for 18 h against the same buffer.

An aliquot of the dialyzed extract containing 150 mg of the protein was loaded onto a Sephadex A25® anion exchange column (Pharmacia, Uppsala, Sweden) with bed dimensions of 70 cm length and 2.5 cm diameter. The sample was eluted isocratically with buffer B at a linear flow rate of 10 cm/h. Fractions containing HIV protease activity (see below for assay description) were combined, and soluble protein was precipitated by the addition of saturated aqueous $(NH_4)_2SO_4$ to yield a total $(NH_4)_2SO_4$ concentration of 85% saturation. Precipitated protein was removed by centrifugation and the resulting pellet was dissolved in buffer C {50 mM 2-(4-morpholino)ethanesulfonic acid (MES), pH 5.5; 150 mM NaCl; 1 mM DTT; 1 mM EDTA; 10% glycerol}. This preparation was dialyzed for 18 h against buffer C, and then frozen at −70°. All crude extracts were purified by chromatography in aliquots containing 150 mg of protein in the same manner as described above. The final preparations from each batch were pooled, divided into 34 μL aliquots and stored at −70°. The final protein recovered from a 20 L fermentation was typically 300 mg with a specific activity for HIV protease of 18.2 mmoles of substrate cleaved/min/mg.

The aliquots were diluted to 1/38 of the original concentration with buffer, see below, prior to use (i.e. the enzyme working solution).

Substrate: VSFNFPQITL-NH$_2$, MW 1164, see Krausslich et al., Proc. Natl. Acad. Sci. USA, 86, 807 (1989), was used as substrate. The substrate was made into 10 mM stock in DMSO and stored at 4°. Prior to use, the stock was diluted with buffer to give a 400 μM solution (i.e. the substrate working solution).

Buffer: MES (100 mM), KCl (300 mM) and EDTA (5 mM) were dissolved in distilled H$_2$O (90 mL) and the solution was adjusted to pH 5.5 with concentrated aqueous NaOH. The latter solution was diluted to 100 mL with H$_2$O to give the buffer.

Procedure: (1) The assay mixture was prepared by mixing 20 μL of the substrate working solution, 10 μL of the solution of the test compound in 10% DMSO and 10 μL of the enzyme working solution. (2) The assay mixture was incubated at 37° for 30 min. (3) The reaction was quenched by adding 200 μL of 2% aqueous trifluoroacetic acid. (4) The substrate and products (i.e. VSFNF and PQITL-NH$_2$) were separated by subjecting 100 μL of the quenched assay mixture to HPLC using a Perkin-Elmer 3×3 CRC8 column (Perkin Elmer Inc., Norwalk, Conn., USA) with a stepwise gradient at a flow rate of 4 mL/min. The gradient is as follows:

0.0–0.5 minutes, 70% A/30% B;

0.5–3.0 minutes, 67% A/33% B;

3.0–5.0 minutes, 20% A/80% B;

5.0–6.5 minutes, 70% A/30% B;

where A is 3 mM sodium dodecyl sulfate/0.05% H$_3$PO$_4$ in H$_2$O and B is 0.05% H$_3$PO$_4$ in acetonitrile. Elution was monitored at 210 nM. (5) A control, which was the assay mixture without the test compound, was subjected simultaneously to steps 2 to 4.

Inhibition Studies: Cleavage products and remaining parent substrate were quantified by either peak height or by integration of the appropriate HPLC peaks. Substrate conversion was calculated using the following relationship:

$$\% \text{ Conversion} = \frac{\text{Sum of peak height or peak area of products}}{\text{Sum of peak height or peak area of substrate and products}} \times 100$$

Enzyme inhibition of the test compound was calculated as follows:

$$\% \text{ Inhibition} = 100 - \frac{\% \text{ Conversion for assay mixture}}{\% \text{ Conversion of control}} \times 100$$

The concentration of the test compound which causes a 50% inhibition of the HIV-protease, i.e. the IC$_{50}$, was determined as follows: The percent inhibition of the enzyme was determined for a minimum of three different concentrations of the test compound. Thereafter, the IC$_{50}$ was determined graphically by plotting the percent inhibition of the enzyme against the concentration of the test compound.

The IC$_{50}$'s of some exemplified compounds of formula 1, as determined in the recombinant HIV protease HPLC assay, are listed in Table IV, following the next example.

EXAMPLE 12

The following protocol, used for screening antiviral effects of the compounds of formula 1, is adapted from a plaque assay utilizing HTLV-I transformed cells, previously reported by Harada et al., supra. HTLV-I transformed cells are used because of the rapidity with which HIV will replicate in the cells.

1. The test compound is dissolved in dimethylsulfoxide to a concentration of 5 mg/mL. The resultant solution can be stored at 4° until use.

2. The resultant solution is diluted in RPMI 1640 (Gibco Laboratories, St. Lawrence, Mass., USA) to four times (4×) the final concentration which is to be tested. Once diluted in RPMI 1640, the solution is used in the cell culture assay within 4 h.

3. The 4× solution (50 μL) is added to triplicate wells of a 96 well flat bottomed microtiter plate. RPMI (50 μL) also is added to control wells.

4. C8166 cells (5×10$^4$) in 50 μL of HEPES-buffered RPMI 1640 (pH=7.2), 10% heat inactivated fetal calf serum (FCS), 12.5 μL/mL gentamicin (complete media) are added to all wells.

5. Fifty times TCID$_{50}$ of H9/HTLV-IIIB stock (stored in liquid nitrogen as cell culture supernatant in 50% FCS) in 100 μL of complete media is added to all wells. Infectious titer of virus stocks are as previously determined by end point dilution on C8166 cells. Titer of stocks are stable for 6–12 months when stored at −193°.

6. Microtiter plates are then placed on level shelves of a 37°, 5% CO$_2$ humidified incubator for 72 h.

7. Plates are then removed and centers of syncytia are counted in each well by low power phase contrast light microscopy. Each cluster of cells which shows evidence of any syncytia formation is counted as one center of syncytia. Control wells should have between 25 and 75 centers of syncytia per well.

8. Percent inhibition of syncytia formation is calculated by the formula:

$$\% \text{ inhibition} = 100 \times \frac{\left(\begin{array}{c}\text{\# syncytial} \\ \text{centers in} \\ \text{control wells}\end{array}\right) - \left(\begin{array}{c}\text{\# syncytial} \\ \text{centers in} \\ \text{test wells}\end{array}\right)}{\left(\begin{array}{c}\text{\# syncytial centers in} \\ \text{control wells}\end{array}\right)}$$

The concentration of the test compound which causes a 50% inhibition of syncytia formation, i.e. the EC$_{50}$, is determined by using the technique of serial dilution of the working solution at step 3 and by using non-linear regression analysis (SAS® program) to graphically plot the observed percent inhibition of syncytia formation against the various concentrations of the test compound.

In the following Table IV, assay results are listed for exemplified compounds of formula 1 from the recombinant HIV protease HPLC assay of example 10, i.e. IC$_{50}$(nM), and from the plaque assay of example 11, i.e. EC$_{50}$ (nM). Note that for some of the compounds listed in Table IV, the EC$_{50}$'s have not been determined (ND).

TABLE IV

| ENTRY NO. | COMPOUND | IC$_{50}$ (nM) | EC$_{50}$ (nM) |
|---|---|---|---|
| 1 | N-tert-butyl-1-{3(S)-(benzyloxycarbonylamino)-2(R)-hydroxy-4-(4-fluorophenyl)butyl}-4(R)-(phenylthio)piperidine-2(S)-carboxamide (described in example 5) | 9.5 | ND |
| 2 | N-tert-butyl-1-{3(S)-(benzyloxycarbonylamino)-2(R)-hydroxy-4-phenylbutyl}-4(R)-phenylpiperidine-2(S)-carboxamide (Table I, entry 1) | 400 | ND |

TABLE IV-continued

| ENTRY NO. | COMPOUND | IC$_{50}$ (nM) | EC$_{50}$ (nM) |
|---|---|---|---|
| 3 | N-tert-butyl-1-{3(S)-(benzyloxycarbonylamino)-2(R)-hydroxy-4-phenylbutyl}-4(R)-benzylpiperidine-2(S)-carboxamide (Table I, entry 2) | 460 | ND |
| 4 | N-tert-butyl-1-{3(S)-(benzyloxycarbonylamino)-2(R)-hydroxy-4-phenylbutyl}-4(R)-(phenylsulfonyl)piperidine-2(S)-carboxamide (Table I, entry 3) | 30 | 1400 |
| 5 | N-tert-butyl-1-{3(S)-(benzyloxycarbonylamino)-2(R)-hydroxy-4-phenylbutyl}-4(R)-(phenylthio)piperidine-2(S)-carboxamide (Table I, entry 4) | 10 | 800 |
| 6 | N-tert-butyl-1-{3(S)-(benzyloxycarbonylamino)-2(R)-hydroxy-4-phenylbutyl}-4(R)-phenoxypiperidine-2(S)-carboxamide (Table I, entry 5) | 53 | ND |
| 7 | N-tert-butyl-1-{3(S)-(benzyloxycarbonylamino)-2(R)-hydroxy-4-phenylbutyl}-4(R)-cylohexylpiperidine-2(S)-carboxamide (Table I, entry 7) | 2100 | ND |
| 8 | N-tert-butyl-1-{-3(S)-{{N-benzyloxycarbonyl)valyl}amino}-2(R)-hydroxy-4-phenylbutyl}-4(R)-(phenylthio)piperidine-2(S)-carboxamide (Table II, entry 1) | 3.9 | 13 |
| 9 | N-tert-butyl-1-{3(S)-{{N-(benzyloxycarbonyl)asparaginyl}amino}-2(R)-hydroxy-4-phenylbutyl}-4(R)-(phenylthio)piperidine-2(S)-carboxamide (Table II, entry 2) | 4 | 43 |
| 10 | N-tert-butyl-1-{3(S)-{{N-(benzyloxycarbonyl)valyl}amino}-2(R)-hydroxy-4-phenylbutyl}-4(R)-phenylpiperidine-2(S)-carboxamide (Table II, entry 4) | 3.1 | 90 |
| 11 | N-tert-butyl-1-{3(S)-{{N-(benzyloxycarbonyl)isoleucyl}amino}-2(R)-hydroxy-4-phenylbutyl}-4(R)-phenylpiperidine-2(S)-carboxamide (Table II, entry 5) | 3.7 | 700 |
| 12 | N-tert-butyl-1-{3(S)-{N-(benzyloxycarbonyl)asparaginyl}amino}-2(R)-hydroxy-4-phenylbutyl}-4(R)-phenylpiperidine-2(S)-carboxamide (Table II, entry 6) | 6.3 | 150 |
| 13 | N-tert-butyl-1-{3(S)-{N-(benzyloxycarbonyl)valyl}amino}-2(R)-hydroxy-4-phenylbutyl}-4(R)-benzylpiperidine-2(S)-carboxamide (Table II, entry 7) | 4.1 | 40 |
| 14 | N-tert-butyl-1-{3(S)-{N-(benzyloxycarbonyl)valyl}amino}-2(R)-hydroxy-4-phenylbutyl}-4(R)-(phenylsulfonyl)piperidine-2(S)-carboxamide (Table II, entry 8) | 2.3 | 40 |
| 15 | N-tert-butyl-1-{3(S)-{N-(benzyloxycarbonyl)asparaginyl}amino}-2(R)-hydroxy-4-phenylbutyl}-4(R)-(phenylsulfonyl)piperidine-2(S)-carboxamide (Table II, entry 9) | 2.9 | 1270 |
| 16 | N-tert-butyl-1-{3(S)-{N-(benzyloxycarbonyl)valyl}amino}-2(R)-hydroxy-4-phenylbutyl}-4(R)-phenoxypiperidine-2(S)-carboxamide (Table II, entry 10) | 2.7 | 150 |
| 17 | N-tert-butyl-1-{3(S)-{N-(benzyloxycarbonyl)asparaginyl}amino}-2(R)-hydroxy-4-phenylbutyl}-4(R)-phenoxypiperidine-2(S)-carboxamide (Table II, entry 11) | 2.5 | 42 |
| 18 | N-tert-butyl-1-{3(S)-{N-(benzyloxycarbonyl)valyl}amino}-2(R)-hydroxy-4-phenylbutyl}-4(R)-(2-pyridinyloxy)piperidine-2(S)-carboxamide (Table II, entry 12) | 1.8 | 56 |
| 19 | N-tert-butyl-1-{3(S)-{N-(benzyloxycarbonyl)valyl}amino}-2(R)-hydroxy-4-phenylbutyl}-4(R)-cyclohexylpiperidine-2(S)-carboxamide (Table II, entry 13) | 8 | 200 |
| 20 | N-tert-butyl-1-{2(R)-hydroxy-4-phenyl-3(S)-{{N-(2-quinolinylcarbonyl)valyl}amino}butyl}-4(R)-(phenylthio)piperidine-2(S)-carboxamide (Title compound of example 7) | 3.1 | 12 |
| 21 | N-tert-butyl-1-{2(R)-hydroxy-4-phenyl-3(S)-{{N-(2-quinolinylcarbonyl)asparaginyl}amino}butyl}-4(R)-phenoxypiperidine-2(S)-carboxamide (Table III, entry 1) | 5.4 | 15 |
| 22 | N-tert-butyl-1-{2(R)-hydroxy-4-phenyl-3(S)-{{N-(2-quinolinylcarbonyl)asparaginyl}amino}butyl}-4(R)-(phenylsulfonyl)piperidine-2(S)-carboxamide (Table III, entry 2) | 4.7 | 450 |
| 23 | N-tert-butyl-1-{2(R)-hydroxy-4-phenyl-3(S)-{{N-(2-quinolinylcarbonyl)asparaginyl}amino}butyl}-4(R)-(phenylthio)piperidine-2(S)-carboxamide (Table III, entry 3) | 1.8 | 10 |
| 24 | N-tert-butyl-1-{2(R)-hydroxy-4-phenyl-3(S)-{{N-(2-naphthalenylcarbonyl)valyl}amino}butyl}-4(R)-(phenylthio)piperidine-2(S)-carboxamide (Table III, entry 4) | 2.3 | 16 |
| 25 | N-tert-butyl-1-{2(R)-hydroxy-3(S)-{{N-(2-naphthalenylcarbonyl)asparaginyl}amino}-4-phenylbutyl}-4(R)-(phenylthio)piperidine-2(S)-carboxamide (Table III, entry 5) | 1.9 | 33 |
| 26 | N-tert-butyl-1-{3(S)-{{N-(benzyloxycarbonyl)valyl}amino}-2(R)-hydroxy-4-(4-fluorophenyl)butyl}-4(R)-(phenylthio)piperidine-2(S)-carboxamide (described in example 6) | 3.5 | 24 |
| 27 | N-tert-butyl-1-{2(R)-hydroxy-4-phenyl-3(S)-{{N-{(2-pyridinylmethoxy)carbonyl}isoleucyl}amino}butyl}-4(R)-phenylpiperidine-2(S)-carboxamide (Title compound of example 8) | 4.9 | 500 |
| 28 | N-tert-butyl-1-{3(S)-(benzyloxycarbonylamino-2(R)-hydroxy-4-phenylbutyl}-4(R)-(2-pyridinylthio)piperidine-2(S)-carboxamide (Table I, entry 8) | 16 | 500 |
| 29 | N-tert-butyl-1-{3(S)-(benzyloxycarbonylamino-2(R)-hydroxy-4-phenylbutyl}-4(R)-(4-pyridinylthio)piperidine-2(S)-carboxamide (Table I, entry 9) | 8 | 140 |
| 30 | N-tert-butyl-1-{3(S)-(benzyloxycarbonylamino)-2(R)-hydroxy-4-phenylbutyl}-4(R)-(2-pyrimidinylthio)piperidine-2(S)-carboxamide (Table I, entry 10) | 19 | 822 |
| 31 | N-tert-butyl-1-{3(S)-(benzyloxycarbonylamino)-2(R)-hydroxy-4-phenylbutyl}-4(R)-(4,6-dimethyl-2-pyrimidinylthio)-piperidine-2(S)-carboxamide (Table I, entry 11) | 12 | 290 |
| 32 | N-tert-butyl-1-{3(S)-(benzyloxycarbonylamino)-2(R)-hydroxy-4-phenylbutyl}-4(R)-(benzylthio)piperidine-2(S)-carboxamide (Table I, entry 12) | 10 | ND |
| 33 | N-tert-butyl-1-{3(S)-{{N-(benzyl- | 3.2 | 11 |

TABLE IV-continued

| ENTRY NO. | COMPOUND | IC$_{50}$ (nM) | EC$_{50}$ (nM) |
|---|---|---|---|
| | oxycarbonyl)valyl}amino}-2(R)-hydroxy-4-phenylbutyl}-4(R)-(2-pyridinylthio)piperidine-2(S)-carboxamide (Table II, entry 14) | | |
| 34 | N-tert-butyl-1-{3(S)-{{N-(benzyl-oxycarbonyl)valyl}amino}-2(R)-hydroxy-4-phenylbutyl}-4(R)-(4-pyridinylthio)piperidine-2(S)-carboxamide (Table II, entry 15) | 2.5 | 11 |
| 35 | N-tert-butyl-1-{3(S)-{{N-(benzyl-oxycarbonyl)valyl}amino}-2(R)-hydroxy-4-phenylbutyl}-4(R)-(2-pyrimidinylthio)piperidine-2(S)-carboxamide (Table II, entry 16) | 3.7 | 15 |
| 36 | N-tert-butyl-1-{3(S)-{{N-(benzyl-oxycarbonyl)valy}amino}-2(R)-hydroxy-4-phenylbutyl}-4(R)-(4,6-dimethyl-2-pyrimidinylthio)piperidine-2(S)-carboxamide (Table II, entry 17) | 3.0 | 9 |
| 37 | N-tert-butyl-1-{3(S)-{{N-(benzyl-oxycarbonyl)valyl}amino}-2(R)-hydroxy-4-phenylbutyl}-4(R)-(benzylthio)piperidine-2(S)-carboxamide (Table II, entry 18) | 2.3 | 7 |
| 38 | N-tert-butyl-1-{2(R)-hydroxy-3(S)-{N-{{N-methyl-N-(2-pyridinyl-methyl)amino}carbonyl}valyl}-4-phenylbutyl}-4(R)-(phenylthio)-piperidine-2(S)-carboxamide (Title compound of example 9) | 4.3 | 14 |

Other compounds of formula 1 prepared by the processes disclosed herein are listed in Tables V, VI and VII together with characterizing mass spectral data and the assay results for the compounds from the recombinant HIV protease HPLC assay of example 11, i.e. IC$_{50}$ (nM) and from the plaque assay of example 12, i.e. EC$_{50}$ (nM).

TABLE V

| ENTRY No. | Compound of formula 1 having the formula N-tert-butyl-1-{2(R)-hydroxy-4-phenyl-3(S)-{{N-(2-quinol-ylinylcarbonyl)valyl}-amino}butyl}-Y-piperidine-2-carboxamide wherein Y is as designated hereinbelow | FAB/MS (m/z) (M + H)$^+$ | IC$_{50}$ (nM) | EC$_{50}$ (nM) |
|---|---|---|---|---|
| 1 | 4(R)-(2-pyrimidinylthio) | 712 | 3.6 | 7 |
| 2(S) | 4(R)-{(4-pyridinylmethyl)thio} | 725 | 2.8 | 4 |
| 3 | 4(R)-(2-pyridinylmethoxy) | 709 | 3.9 | 24 |
| 4 | 4(R)-{(4,6-dimethyl-2-pyrimidinyl)thio} | 740 | 2.7 | 8 |

| ENTRY No. | Compound of formula 1 having the formula N-tert-butyl-1-{2(S)(R)-hydroxy-4-phenyl-3(S)-{{N-(2-quinol-ylinylcarbonyl)valyl}-amino}butyl}-Y-piperidine-2-carboxamide wherein Y is as designated hereinbelow | FAB/MS (m/z) (M + H)$^+$ | IC$_{50}$ (nM) | EC$_{50}$ (nM) |
|---|---|---|---|---|
| 5 | 4(R)-(4-pyridinylthio) | 711 | 1.5 | 3 |
| 6 | 4(R)-(2-pyridinylthio) | 711 | 1.9 | 4 |
| 7 | 4(R)-phenoxy | 694 | 3.4 | 14 |
| 8 | 4(R)-{(3-pyridinylmethyl)thio} | 725 | 2.2 | 3 |
| 9 | 4(R)-{(2-pyridinylmethyl)thio} | 725 | 4.2 | 5 |
| 10 | 4(R)-(2-pyrimidinyloxy) | 696 | 3.2 | 25 |
| 11 | 4(R)-{(4,6-dimethyl-2-pyrimidinyl)oxy} | 724 | 4.0 | 20 |
| 12 | 4(R)-{(4-methyl-2-pyrimidinyl)oxy} | 710 | 4.5 | 44 |
| 13 | 4(R)-{(2,6-dimethyl-4-pyrimidinyl)oxy} | 724 | 3.6 | 17 |
| 14 | 4(R)-(phenylsulfonyl) | 756 | 2.9 | 23 |
| 15 | 4(R)-{(4-fluorophenyl)oxy} | 712 | 2.6 | 22 |
| 16 | 4(R)-(4-pyridinylmethoxy) | 709 | 4.2 | 22 |
| 17 | 4(R)-{(2-pyridinylmethyl)sulfonyl} | 757 | 2.4 | 33 |
| 18 | 4(R)-{(3-pyridinylmethyl)sulfonyl} | 757 | 1.8 | 67 |
| 19 | 4(R)-{(4-pyridinylmethyl)sulfonyl} | 757 | 4.6 | 73 |
| 20 | 4(R)-(2-pyridinylsulfonyl) | 743 | 1.7 | 13 |

| ENTRY No. | Compound of formula 1 having the formula N-tert-butyl-1-{2(R)-hydroxy-4-phenyl-3(S)-{{N-(2-quinol-ylinylcarbonyl)valyl}-amino}butyl}-Y-piperidine-2(S)-carboxamide wherein Y is as designated hereinbelow | FAB/MS (m/z) (M + H)$^+$ | IC$_{50}$ (nM) | EC$_{50}$ (nM) |
|---|---|---|---|---|
| 21 | 4(R)-(4-pyridinylsulfonyl) | 743 | 1.7 | 25 |
| 22 | 4(R)-{(2,6-dimethyl-4-pyrimidinyl)thio} | 740 | 2.4 | 11 |
| 23 | 4(R)-{(4-methyl-2-pyrimidinyl)thio} | 726 | 2.8 | 16 |
| 24 | 4(R)-(3-pyridinylmethoxy) | 709 | 3.7 | 53 |

TABLE VI

| ENTRY No. | Compound of formula 1 having the formula N-tert-butyl-1-{2(R)-hydroxy-4-phenyl-3(S)-{{N-(2-quinol-ylinylcarbonyl)B}amino}-butyl}-Y-piperidine-2(S)-carboxamide wherein B and Y are as designated hereinbelow | | FAB/MS (m/z) (M + H)$^+$ | IC$_{50}$ (nM) | EC$_{50}$ (nM) |
|---|---|---|---|---|---|
| | B | Y | | | |
| 1 | -tert-butylglycyl | 4(R)-(phenylthio) | 724 | 3.0 | 12 |
| 2 | asparaginyl | 4(R)-{(4,6-dimethyl-2-pyrimidinyl)}thio | 755 | 2.2 | 42 |
| 3 | asparaginyl | 4(R)-(2-pyrimidinylthio) | 727 | 2.1 | 60 |
| 4 | -(N$^4$-methyl)asparaginyl | 4(R)-phenoxy | 723 | 3.7 | 13 |
| 5 | -tert-butylglycyl | 4(R)-{(3-pyridinylmethyl)thio} | 740 | 2.2 | 8 |
| 6 | threonyl | 4(R)-(phenylsulfonyl) | 744 | 2.6 | 61 |
| 7 | -tert-butylglycyl | 4(R)-(4-pyridinylsulfonyl) | 757 | 2.1 | 29 |
| 8 | -tert-butylglycyl | 4(R)-(2-pyridinylsulfonyl) | 757 | 2.9 | 44 |

TABLE VII

| ENTRY No. | Compound of formula 1 having the formula N-tert-butyl-1-{3(S)-{{X}-amino}-2(R)-hydroxy-4-phenylbutyl}-Y-piperidine-2(S)-carboxamide wherein X and Y are as designated below | | FAB/MS (m/z) (M + H)+ | IC$_{50}$ (nM) | EC$_{50}$ (nM) |
|---|---|---|---|---|---|
| | X | Y | | | |
| 1* | (2,6-dimethylphenoxy)acetyl | 4(R)-{(3-pyridinylmethyl)thio} | 633 | 2.7 | 35 |
| 2 | (2,4,6-trimethylphenoxy)acetyl | 4(R)-(4-pyridinylthio) | 633 | 3.7 | 47 |
| 3 | phenoxyacetyl | 4(R)-(4-pyridinylthio) | 591 | 34 | ND |
| 4 | (2,6-dimethylphenoxy)acetyl | 4(R)-(4-pyridinylthio) | 619 | 3.1 | 20 |
| 5 | (2-methylphenoxy)acetyl | 4(R)-(4-pyridinylthio) | 605 | 6.2 | 140 |
| 6 | (2,4-dichlorophenyl)carbonyl | 4(R)-(4-pyridinylthio) | 629 | 5.4 | 340 |
| 7 | (2,5-dichlorophenyl)carbonyl | 4(R)-(4-pyridinylthio) | 629 | 9.8 | 360 |
| 8 | (2,6-difluorophenyl)carbonyl | 4(R)-(4-pyridinylthio) | 597 | 14 | 340 |
| 9 | (5-fluoro-2-methylphenyl)carbonyl | 4(R)-(4-pyridinylthio) | 593 | 6.8 | ND |

*Preparation of the compound of entry 1 is described in example 10.

Other compounds of formula 1 include:

N-tert-butyl-1-{2(R)-hydroxy-4-phenyl-3(S)-{{N-(2-quinolinylcarbonyl)asparaginyl}amino}butyl}-4(R)-(4-pyridinylthio)piperidine-2(S)-carboxamide N-tert-butyl-1-{4-(4-fluorophenyl)-2(R)-hydroxy-3(S)-{{N-(2-naphthalenylcarbonyl)valyl}amino}butyl}-4(R)-(2-pyrimidinylthio)piperidine-2(S)-carboxamide N-tert-butyl-1-{2(R)-hydroxy-4-phenyl-3(S)-{{N-(2-pyridinylcarbonyl)valyl}amino}butyl}-4(R)phenoxypiperidine-2(S)-carboxamide N-tert-butyl-1-{2(R)-hydroxy-4-phenyl-3(S)-{{N-(2-pyridinylcarbonyl)asparaginyl}amino}butyl}-4(R)phenoxypiperidine-2(S)-carboxamide

We claim:

1. A compound of formula 1

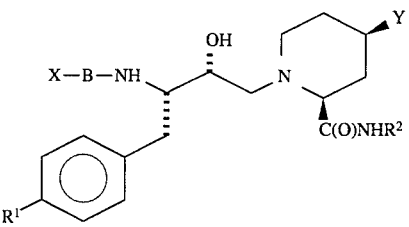

wherein

X is $R^3OC(O)$, $R^3C(O)$ or $R^3NR^4C(O)$ wherein $R^3$ is 2-quinolinyl or 3-quinolinyl, and $R^4$ is hydrogen or lower alkyl;

B is absent or the divalent radical —NHCHR$^5$C(O)— wherein R$^5$ is lower alkyl; lower cycloalkyl; (lower cycloalkyl)-(lower alkyl); phenylmethyl; or lower alkyl monosubstituted with hydroxy, carboxy, lower alkoxycarbonyl, aminocarbonyl, (lower alkyl)aminocarbonyl or di(lower alkyl)aminocarbonyl;

$R^1$ is hydrogen, halo, hydroxy, lower alkyl or lower alkoxy;

$R^2$ is lower alkyl; and

Y is lower alkyl; lower cycloalkyl; phenyl or phenyl monosubstituted with halo, hydroxy, lower alkyl or lower alkoxy; phenylmethyl or phenylmethyl monosubstituted with halo, hydroxy, lower alkyl or lower alkoxy; or Y is W(CH$_2$)$_n$Z wherein W is oxo, thio, sulfinyl or sulfonyl, Z is lower alkyl; phenyl or phenyl monosubstituted with halo, hydroxy, lower alkyl or lower alkoxy; or (Het); and n is zero or one;

wherein the term "lower alkyl" as used herein, either alone or in combination with another radical, means a straight chain alkyl radical containing one to six carbon atoms or a branched chain alkyl radical containing three to four carbon atoms;

wherein the term "lower cycloalkyl" as used herein, either alone or in combination with another radical, means a saturated cyclic hydrocarbon radical containing from three to six carbon atoms;

wherein the term "lower alkoxy" as used herein means a straight chain alkoxy radical containing one to six carbon atoms or a branched chain alkoxy radical containing three to four carbon atoms;

wherein the term "halo" as used herein means a halo radical selected from bromo, chloro, fluoro and iodo; and, wherein (Het) as used herein means a monovalent radical derived by removal of a hydrogen from a five or six membered saturated or unsaturated heterocycle selected from the group consisting of furan, thiophene, pyrrolidine, tetrahydrofuran, thiazolidine, pyrrole, 1H-imidazole, 1-methyl-1H-imidazole, isoxazole, thiazole, 2-methylthiazole, 2-aminothiazole, piperidine, 1,4-dioxane, morpholine, pyridine, 2-methylpyridine, pyrimidine, 4-methylpyrimidine, 2,4-dimethylpyrimidine, 2,6-dimethylpyrimidine and 4,6-dimethylpyrimidine;

or a therapeutically acceptable acid addition salt thereof.

2. A compound as defined in claim 1 wherein X is $R^3OC(O)$, $R^3C(O)$ or $R^3NR^4C(O)$ wherein $R^3$ is 2-quinolinyl, and $R^4$ is hydrogen or lower alkyl;

B is absent or is the divalent radical —NHCHR$^5$C(O)— wherein $R^5$ is lower alkyl, or lower alkyl monsubstituted with hydroxy, lower alkoxycarbonyl, aminocarbonyl, (lower alkyl)aminocarbonyl or di(lower alkyl)aminocarbonyl;

$R^1$ is hydrogen, chloro, bromo or fluoro;

$R^2$ is 1-methylethyl, 2-methylpropyl or 1,1-dimethylethyl; and

Y is phenyl, 4-chlorophenyl, 4-bromophenyl, 4-fluorophenyl, 4-methylphenyl, 4-methoxyphenyl, phenylmethyl, (4-fluorophenyl)methyl or (4-methylphenyl)methyl; or Y is W(CH$_2$)$_n$Z wherein W and n are as defined in claim 1 and Z is lower alkyl, phenyl, 2-furyl, 2-thienyl, 2-pyridinyl, 3-pyridinyl, 4-pyridinyl, 4-thiazolyl, 2-pyrimidinyl, 4-methyl-2-pyrimidinyl, 4,6-dimethyl-2-pyrimidinyl or 2,6-dimethyl-4-pyrimidinyl; or a therapeutically acceptable acid addition salt thereof.

3. A compound as defined in claim 2 wherein X is 2-quinolinylcarbonyl;

B is absent or the divalent radical —NHCHR$^5$C(O)— wherein R$^5$ is 1-methylethyl, 1,1-dimethylethyl, 1-methylpropyl, 2-methylpropyl, 1-hydroxyethyl, (methoxycarbonyl)methyl, (ethoxycarbonyl)methyl, (aminocarbonyl)methyl or {(methylamino)carbonyl}methyl; R$^1$ is hydrogen or fluorine; R$^2$ is 2-methylpropyl or 1,1-dimethylethyl; and Y is phenyl, 4-chlorophenyl, 4-fluorophenyl, 4-methoxyphenyl, benzyl, (4-methoxyphenyl)methyl, 2-methylpropoxy, phenoxy, 2-pyridinyloxy, 3-pyridinyloxy, 4-pyridinyloxy, 2-pyrimidinyloxy, (4-methyl-2-pyrimidinyl)oxy, (4,6-dimethyl-2-pyrimidinyl)oxy, (2,6-dimethyl-4-pyrimidinyl)oxy, benzyloxy, 2-pyridinylmethoxy, 3-pyridinylmethoxy, 4-pyridinylmethoxy, 4-thiazolylmethoxy, phenylthio, phenylsulfinyl, phenylsulfonyl, 2-pyridinylthio, 3-pyridinylthio, 4-pyridinylthio, 2-pyrimidinylthio, (4-methyl-2-pyrimidinyl)thio, (2,6-dimethyl-4-pyrimidinyl)thio, (4,6-dimethyl-2-pyrimidinyl)thio, benzylthio, benzylsulfinyl, benzylsulfonyl, (2-pyridinylmethyl)thio, (3-pyridinylmethyl)thio or (4-pyridinylmethyl)thio; or a therapeutically acceptable acid addition salt.

4. A compound as defined in claim 3 wherein X is 2-quinolinylcarbonyl;

B is valyl, tert-butylglycyl, isoleucyl, threonyl or asparaginyl; R$^1$ is hydrogen or fluorine; R$^2$ is 1,1-dimethylethyl; and Y is phenyl, benzyl, phenoxy, 2-pyrimidinyloxy, (2,6-dimethyl-4-pyrimidinyl)oxy, 2-pyridinylmethoxy, 3-pyridin-ylmethoxy, 4-pyridinylmethoxy, phenylthio, phenylsulfinyl, phenylsulfonyl, 2-pyridinylthio, 3-pyridinylthio, 4-pyridinylthio, 2-pyrimidinylthio (4,6-dimethyl-2-pyrimidinyl)thio, (2-pyridinylmeth-yl)thio, (3-pyridinylmethyl)thio or 4-(pyridinyl-methyl)thio; or a therapeutically acceptable acid addition salt thereof.

5. A compound selected from the group consisting of:

N-tert-butyl-1-{2(R)-hydroxy-4-phenyl-3(S)-{{N-(2-quinolinylcarbonyl)valyl}amino}butyl}-4(R)-(phenylthio)piperidine-2(S)-carboxamide, N-tert-butyl-1-{2(R)-hydroxy-4-phenyl-3(S)-{{N-(2-quinolinylcarbonyl)asparaginyl}amino}butyl}-4(R)-phenoxypiperidine-2(S)-carboxamide, N-tert-butyl-1-{2(R)-hydroxy-4-phenyl-3(S)-{{N-(2quinolinylcarbonyl)asparaginyl}amino}butyl}-4(R)-(phenylsulfonyl)piperidine-2(S)-carboxamide, N-tert-butyl-1-{2(R)-hydroxy-4-phenyl-3(S)-{{N-(2-quinolinylcarbonyl)asparaginyl}amino}butyl}-4(R)-(phenylthio)piperidine-2(S)-carboxamide, N-tert-butyl-1-{2(R)-hydroxy-4-phenyl-3(S)-{{N-(2-quinolinylcarbonyl)valyl}amino}butyl}-4(R)-(2-pyrimidinylthio)piperidine-2(S)-carboxamide, N-tert-butyl-1-{2(R)-hydroxy-4-phenyl-3(S)-{{N-(2quinolinylcarbonyl)valyl}amino}butyl}-4(R)-{(4-pyridinylmethyl)thio}piperidine-2(S)-carboxamide, N-tert-butyl-1-{2(R)-hydroxy-4-phenyl-3(S)-{{N-(2-quinolinylcarbonyl)valyl}amino}butyl}-4(R)-(2-pyridinylmethoxy)piperidine-2(S)-carboxamide, N-tert-butyl-1-{2(R)-hydroxy-4-phenyl-3(S)-{{N-(2-quinolinylcarbonyl)valyl}amino}butyl}-4(R)-{(4,6-dimethyl-2-pyrimidinyl)thio}piperidine-2(S)-carboxamide, N-tert-butyl-1-{2(R)-hydroxy-4-phenyl-3(S)-{{N-(2-quinolinylcarbonyl)valyl}amino}butyl}-4(R)-(4-pyridinylthio)piperidine-2(S)-carboxamide, N-tert-butyl-1-{2(R)-hydroxy-4-phenyl-3(S)-{{N-(2-quinolinylcarbonyl)valyl}amino}butyl}-4(R)-(2-pyridinylthio)piperidine-2(S)-carboxamide, N-tert-butyl-1-{2(R)-hydroxy-4-phenyl-3(S)-{{N-(2-quinolinylcarbonyl)valyl}amino}butyl}-4(R)-phenoxypiperidine-2(S)-carboxamide, N-tert-butyl-1-{2(R)-hydroxy-4-phenyl-3(S)-{{N-(2-quinolinylcarbonyl)valyl}amino}butyl}-4(R)-{(3-pyridinylmethyl)thio}piperidine-2(S)-carboxamide, N-tert-butyl-1-{2(R)-hydroxy-4-phenyl-3(S)-{{N-(2-quinolinylcarbonyl)valyl}amino}butyl}-4(R)-{(2-pyridinylmethyl)thio}piperidine-2(S)-carboxamide, N-tert-butyl-1-{2(R)-hydroxy-4-phenyl-3(S)-{{N-(2-quinolinylcarbonyl)valyl}amino}butyl}-4(R)-(2-pyrimidinyloxy)piperidine-2(S)-carboxamide, N-tert-butyl-1-{2(R)-hydroxy-4-phenyl-3(S)-{{N-(2quinolinylcarbonyl)valyl}amino}butyl}-4(R)-{(4,6-dimethyl-2pyrimidinyl)oxy}piperidine-2(S)-carboxamide, N-tert-butyl-1-{2(R)-hydroxy-4-phenyl-3(S)-{{N-(2-quinolinylcarbonyl)valyl}amino}butyl}-4(R)-{(4-methyl-2-pyrimidinyl)oxy}piperidine-2(S)-carboxamide, N-tert-butyl-1-{2(R)-hydroxy-4-phenyl-3(S)-{{N-(2-quinolinylcarbonyl)valyl}amino}butyl}-4(R)-{(2,6-dimethyl-4-pyrimidinyl)oxy}piperidine-2(S)-carboxamide, N-tert-butyl-1-{2(R)-hydroxy-4-phenyl-3(S)-{{N-(2quinolinylcarbonyl)valyl}amino}butyl}-4(R)-(phenylsulfonyl)piperidine-2(S)-carboxamide, N-tert-butyl-1-{2(R)-hydroxy-4-phenyl-3(S)-{{N-(2-quinolinylcarbonyl)valyl}amino}butyl}-4(R)-{(4-fluorophenyl)oxy}piperidine-2(S)carboxamide, N-tert-butyl-1-{2(R)-hydroxy-4-phenyl-3(S)-{{N-(2-quinolinylcarbonyl)valyl}amino}butyl}-4(R)-(4-pyridinylmethoxy)piperidine-2(S)-carboxamide, N-tert-butyl-1-{2(R)-hydroxy-4-phenyl-3(S)-{{N-(2-quinolinylcarbonyl)valyl}amino}butyl}-4(R)-{(2-pyridinylmethyl)sulfonyl}piperidine-2(S)-carboxamide, N-tert-butyl-1-{2(R)-hydroxy-4-phenyl-3(S)-{{N-(2-quinolinylcarbonyl)valyl}amino}butyl}-4(R)-{(3-pyridinylmethyl)sulfonyl}piperidine-2(S)-carboxamide, N-tert-butyl-1-{2(R)-hydroxy-4-phenyl-3(S)-{{N-(2-quinolinylcarbonyl)valyl}amino}butyl}-4(R)-{(4-pyridinylmethyl)sulfonyl}piperidine-2(S)-carboxamide, N-tert-butyl-1-{2(R)-hydroxy-4-phenyl-3(S)-{{N-(2-quinolinylcarbonyl)valyl}amino}butyl}-4(R)-(2-pyridinylsulfonyl)piperidine-2(S)-carboxamide, N-tert-butyl-1-{2(R)-hydroxy-4-phenyl-3(S)-{{N-(2-quinolinylcarbonyl)valyl}amino}butyl}-4(R)-(4-pyridinylsulfonyl)piperidine-2(S)-carboxamide, N-tert-butyl-1-{2(R)-hydroxy-4-phenyl-3(S)-{{N-(2-quinolinylcarbonyl)valyl}amino}butyl}-4(R)-{(2,6-dimethyl-4-pyrimidinyl)thio}piperidine-2(S)-carboxamide, N-tert-butyl-1-{2(R)-hydroxy-4-phenyl-3(S)-{{N-(2-quinolinylcarbonyl)valyl}amino}butyl}-4(R)-{(4-methyl-2-pyrimidinyl)thio}piperidine-2(S)-carboxamide, N-tert-butyl-1-{2(R)-hydroxy-4-phenyl-3(S)-{{N-(2-quinolinylcarbonyl)valyl}amino}butyl}-4(R)-(3-pyridinylmethoxy)piperidine-2(S)-carboxamide, N-tert-butyl-1-{2(R)-hydroxy-4-phenyl-3(S)-{{N-(2-quinolinylcarbonyl)-tert-butylglycyl}amino}butyl}-4(R)-(phenylthio)piperidine-2(S)-carboxamide, N-tert-butyl-1-{2(R)-hydroxy-4-phenyl-3(S)-{{N-(2-quinolinylcarbonyl)asparaginyl}amino}butyl}-4(R)-{(4,6-dimethyl-2-pyrimidinyl)thio}piperidine-2(S)-carboxamide, N-tert-butyl-1-{2(R)-hydroxy-4-phenyl-3(S)-{{N-(2-quinolinylcarbonyl)asparaginyl}amino}butyl}-4(R)-(2-pyrimidinylthio)piperidine-2(S)-carboxamide, N-tert-butyl-1-{2(R)-hydroxy-4-phenyl-3(S)-{{N-(2-quinolinylcarbonyl)-($N^4$-methyl)asparaginyl}amino}-butyl}-4(R)-phenoxy-piperidine-2(S)-carboxamide, N-tert-butyl-1-{2(R)-hydroxy-4-phenyl-3(S)-{{N-(2-quinolinylcarbonyl)-tert-butylglycyl}amino}butyl}-4(R)-{(3-pyridinylmethyl)thio}piperidine-2(S)-carboxamide, N-tert-butyl-1-{2(R)-hydroxy-4-phenyl-3(S)-{{N-(2-quinolinylcarbonyl)threonyl}amino}butyl}-4(R)-(phenylsulfonyl)piperidine-2(S)-carboxamide, N-tert-butyl-1-{2(R)-hydroxy-4-phenyl-3(S)-{{N-(2-quinolinylcarbonyl)-tert-butylglycyl}amino}butyl}-4(R)-(4-pyridinylsulfonyl)piperidine-2(S)-carboxamide, and N-tert-butyl-1-{2(R)-hydroxy-4-phenyl-3(S)-{{N-(2-quinolinylcarbonyl)-tert-butylglycyl}amino}butyl}-4(R)-(2-pyridinylsulfonyl)piperidine-2(S)-carboxamide.

6. A pharmaceutical composition comprising a compound as recited in claim 1, or a therapeutically acceptable salt thereof, and a pharmaceutically acceptable carrier.

7. A method for treating HIV infections in a human comprising administering thereto an effective amount of a compound as defined in claim 1, or a therapeutically acceptable salt thereof.

8. A pharmaceutical composition comprising a compound as recited in claim 5, or a therapeutically acceptable salt thereof, and a pharmaceutically acceptable carrier.

9. The method for treating HIV infections in a human comprising administering thereto an effective amount of a compound as defined in claim 5, or a therapeutically acceptable salt thereof.

* * * * *